United States Patent [19]
Bock et al.

[11] Patent Number: 5,220,018
[45] Date of Patent: Jun. 15, 1993

[54] CHOLECYSTOKININ ANTAGONISTS

[75] Inventors: Mark G. Bock, Hatfield; Roger M. Freidinger, Lansdale, both of Pa.

[73] Assignee: Merck & Co., Inc., Rahway, N.J.

[21] Appl. No.: 848,790

[22] Filed: Mar. 10, 1992

Related U.S. Application Data

[63] Continuation-in-part of Ser. No. 746,277, Sep. 23, 1991, abandoned, which is a continuation-in-part of Ser. No. 683,007, Apr. 10, 1991, abandoned.

[51] Int. Cl.$^5$ .................. C07D 243/27; A61K 31/55
[52] U.S. Cl. ..................................... 540/509; 514/221
[58] Field of Search .................. 540/509; 514/221

[56] References Cited

U.S. PATENT DOCUMENTS 4,820,834  4/1991  Evans et al. ................ 540/509

FOREIGN PATENT DOCUMENTS 0304223  2/1989  European Pat. Off. ........... 540/509
411668   2/1991  European Pat. Off. ........... 540/509
0434364  6/1991  European Pat. Off. ........... 540/509
0436369  6/1991  European Pat. Off. ........... 540/509
92/01683 2/1992  World Int. Prop. O. .......... 540/509

OTHER PUBLICATIONS

Bradwejn, et al., *Enhanced Sensitivity to Cholecystokinin Tetrapeptide in Panic Disorder*, Soc. Neurosci. Abstr. 14(1), p. 291, (1988).
de Montigny, *Cholecystokinin Tetrapeptide Induces Panic Attacks in Healthy Volunteers*, Soc. Neurosci. Abstr. 14(1), p. 291, (1988).
Bradwejn, et al., *Benzodiazepines Antagonize Cholecystokinin-Induced Activation of Rat Hippocampal Neurones*, Nature 312, p. 22, (1984).
de Montigny, *Cholecystokinin Tetrapeptide Induces Panic-like Attacks in Healthy Volunteers*, Arch. Gen. Psychiatry, 46, pp. 511-517, (1989).
Dourish, et al., *Enhancement of Morphiine Analgesia and Prevention of Morphine Tolerance in the Rat by the Cholecystokinin Antagonist* L-364, 718 Pharm. 147, pp. 469-472, (1988).
Bouthillier, et al., *Long-term Benzodiazepine Treatment Reduces Neuronal Responsiveness to Cholecystokinin: an Electrophysiological Study in the Rat.* Eur. Jour. Pharm. 151, No. 1, pp. 135-138, (1988).
O'Neill et al. *Morphine Induced Analgesia in the Rat Paw Pressure Test is Blocked by CCK and Enhanced by the CCK Antagonist MK-319*, Neuropharmacology 28, No. 3, pp. 243-247 (1989).
Chang, et al., *Biochemical and Pharmacological Characterization of an Extremely Potent and Selective Nonpeptide Cholecystokinin Antagonist*, Proc. Natl. Acad. Sci., 83, pp. 4823-4926 (1986).
Bock, et al., *Benzodiazepine Gastrin and Brain Cholecystokinin Receptor Ligands: L-365,260*, Journal of Medicinal Chemistry, 32, No. 1, pp. 13-16.

*Primary Examiner*—Robert T. Bond
*Attorney, Agent, or Firm*—Mark R. Daniel; Joseph F. DiPrima

[57] ABSTRACT

Benzodiazepine analogs of the formula:

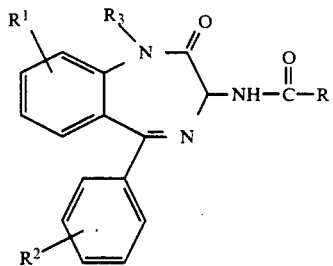

are disclosed which are antagonists of gastrin and cholecystokinin (CCK).

8 Claims, No Drawings

CHOLECYSTOKININ ANTAGONISTS

CROSS-REFERENCE

This is a continuation-in-part application of U.S. Ser. No. 07/764,277 filed on Sep. 23, 1991 now abandoned which is a continuation-in-part application of U.S. Ser. No. 07/683,007 filed on Apr. 10, 1991 now abandoned.

FIELD OF THE INVENTION

This invention relates to the discovery of Benzodiazepine analogs of Formula I for use as antagonists of cholecystokinin (CCK) and gastrin when administered to animals, preferably humans.

BACKGROUND OF THE INVENTION

The Benzodiazepine analogs of Formula I of this invention are useful in treating various diseases caused by an excess of CCK or gastrin. Cholecystokinins (CCK) and gastrin are structurally related neuropeptides which exist in gastrointestinal tissue and in the central nervous system (see, V. Mutt, *Gastrointestinal Hormones*, G. B. J. Glass, Ed., Raven Press, N.Y., p. 169 and G. Nission, ibid, p. 127.

Cholecystokinins include CCK-33, a neuropeptide of thirty-three amino acids in its originally isolated form (see, Mutt and Jorpes, *Biochem. J.* 125, 678 (1971)), its carboxyl terminal octapeptide, CCK-8 (also a naturally-occurring neuropeptide and the minimum fully active sequence), and 39- and 12-amino acid forms. Gastrin occurs in 34-, 17- and 14-amino acid forms, with the minimum active sequence being the C-terminal tetrapeptide, Trp-Met-Asp-Phe-$NH_2$, which is the common structural element shared by both CCK and gastrin.

CCK's are believed to be physiological satiety hormones, thereby possibly playing an important role in appetite regulation (G. P. Smith, *Eating and Its Disorders*, A. J. Stunkard and E. Stellar, Eds, Raven Press, New York, 1984, p. 67), as well as also stimulating colonic motility, gall bladder contraction, pancreatic enzyme secretion, and inhibiting gastric emptying. They reportedly co-exist with dopamine in certain mid-brain neurons and thus may also play a role in the functioning of dopaminergic systems in the brain, in addition to serving as neurotransmitters in their own right (see: A. J. Prange et al., "Peptides in the Central Nervous System", *Ann. Repts. Med. Chem.* 17, 31, 33 [1982] and references cited therein; J. A. Williams, *Biomed. Res.* 3 107 [1982]; and J. E. Morley, *Life Sci.* 30, 479, [1982]).

The primary role of gastrin, on the other hand, appears to be stimulation of the secretion of water and electrolytes in the stomach, and, as such, it is involved in control of gastric acid and pepsin secretion. Other physiological effects of gastrin then include increased mucosal blood flow and increased antral motility. Rat studies have shown that gastrin has a positive trophic effect on the gastric mucosa, as evidenced by increased DNA, RNA and protein synthesis. See e.g. U.S. Ser. No. 452,023.

Antagonists to CCK and to gastrin have been useful for preventing and treating CCK-related and/or gastrin-related disorders of the gastrointestinal (GI) and central nervous (CNS) systems of animals, preferably mammals, and especially those of humans. Just as there is some overlap in the biological activities of CCK and gastrin, antagonists also tend to have affinity for both receptors. In a practical sense, however, there is enough selectivity for the different receptors that greater activity against specific CCK- or gastrin-related disorders can often also be identified.

Selective CCK antagonists are themselves useful in treating CCK-related disorders of the appetite regulatory systems of animals as well as in potentiating and prolonging opiate-mediated analgesia, thus having utility in the treatment of pain [see P. L. Faris et al., *Science* 226, 1215 (1984)]. Selective gastrin antagonists are useful in the modulation of CNS behavior, as a palliative for gastrointestinal neoplasms, and in the treatment and prevention of gastrin-related disorders of the gastrointestinal system in humans and animals, such as peptic ulcers, Zollinger-Ellison syndrome, antral G cell hyperplasia and other conditions in which reduced gastrin activity is of therapeutic value. See e.g. U.S. Pat. No. 4,820,834. It is further expected that the CCK antagonists of Formula I are useful anxiolytic agents particularly in the treatment of panic an anxiety disorders.

Since CCK and gastrin also have trophic effects on certain tumors [K. Okyama, *Hokkaido J. Med. Sci.*, 60, 206–216 (1985)], antagonists of CCK and gastrin are useful in treating these tumors [see, R. D. Beauchamp et al., *Ann. Surg.*, 202, 303 (1985)].

Distinct chemical classes of CCK-receptor antagonists have been reported [R. Freidinger, *Med. Res. Rev.* 9, 271 (1989)]. The first class comprises derivatives of cyclic nucleotides, of which dibutyryl cyclic GMP has been shown to be the most potent by detailed structure-function studies (see, N. Barlas et al., *Am. J. Physiol.*, 242, G 161 (1982) and P. Robberecht et al., *Mol., Pharmacol.*, 17, 268 (1980)).

The second class comprises peptide antagonists which are C-terminal fragments and analogs of CCK, of which both shorter (Boc-Met-Asp-Phe-$NH_2$, Met-Asp-Phe-$NH_2$), and longer (Cbz-Tyr($SO_3$H)-Met-Gly-Trp-Met-Asp-$NH_2$) C-terminal fragments of CCK can function as CCK antagonists, according to recent structure-function studies (see, R. T. Jensen et al., *Biochem. Biophys. Acta.*, 757, 250 (1983), and M. Spanarkel et al., *J. Biol. Chem.*, 258, 6746 (1983)). The latter compound was recently reported to be a partial agonist [see, J. M. Howard et al., *Gastroenterology* 86(5) Part 2, 1118 (1984)].

The third class of CCK-receptor antagonists comprises the amino acid derivatives: proglumide, a derivative of glutaramic acid, and the N-acyl tryptophans including para-chlorobenzoyl-L-tryptophan (benzotript), [see, W. F. Hahne et al., *Proc. Natl. Acad. Sci. U.S.A.*, 78, 6304 (1981), R. T. Jensen et al., *Biochem. Biophys. Acta.*, 761, 269 (1983)]. All of these compounds, however, are relatively weak antagonists of CCK ($IC_{50}$: generally $10^{-4}$M[although more potent analogs of proglumide have been recently reported in F. Makovec et al., *Arzneim-Forsch Drug Res.*, 35 (II), 1048 (1985) and in German Patent Application DE 3522506A1], but down to $10^{-6}$M in the case of peptides), and the peptide CCK-antagonists have substantial stability and absorption problems.

In addition, a fourth class consists of improved CCK-antagonists comprising a nonpeptide of novel structure from fermentation sources [R. S. L. Chang et al., *Science*, 230, 177–179 (1985)] and 3-substituted benzodiazepines based on this structure [published European Patent Applications 167 919, 167 920 and 169 392, B. E. Evans et al., *Proc. Natl. Acad. Sci. U.S.A.*, 83, p. 4918–4922 (1986) and R. S. L. Chang et al, ibid, p. 4923–4926] have also been reported.

No really effective receptor antagonists of the in vivo effects of gastrin have been reported (J. S. Morley, *Gut Pept. Ulcer Proc.*, Hiroshima Symp. 2nd, 1983, p. 1), and very weak in vitro antagonists, such as proglumide and certain peptides have been described [(J. Martinez, *J. Med. Chem.* 27, 1597 (1984)]. Recently, however, pseudopeptide analogs of tetragastrin have been reported to be more effective gastrin antagonists than previous agents [J. Martinez et al., *J. Med. Chem.*, 28, 1874-1879 (1985)].

A new class of Benzodiazepine antagonist compounds has further been reported which binds selectively to brain CCK (CCK-B) and gastrin receptors [see M. Bock et al., *J. Med. Chem.*, 32, 13-16 (1989)]. One compound of interest reported in this reference to be a potent and selective antagonist of CCK-B receptors is (R)-N-(2,3-dihydro-1-methyl-2-oxo-5-phenyl-1H-1,4-benzodiazepin-3-yl)-N$^1$-(3-methylphenyl) urea (See U.S. Pat. No. 4,820,834.) One disadvantage of the new CCK-B compound reported in Bock et al., *J. Med. Chem.*, 32, 13-16 (1989) and U.S. Pat. No. 4,820,834, is that these CCK-B compounds are poorly water soluble.

It is, therefore, an object of the present invention to provide antagonists of CCK and gastrin. If an antagonist compound could be prepared which would bind with the cell surface receptor of CCK or gastrin, then the antagonist compounds of this invention could be used to block the effect of CCK and gastrin. Another object of the present invention is to provide novel CCK and gastrin antagonist compounds which are water soluble. Other objects of the present invention are to provide methods of inhibiting the action of CCK and gastrin through the administration of novel benzodiazepine analog compounds. The above and other object are accomplished by the present invention in the manner more fully described below.

SUMMARY OF THE INVENTION

The present invention provides Benzodiazepine analogs of the formula:

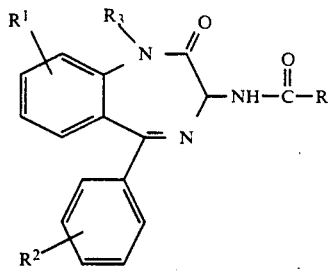

for use as antagonists of CCK and gastrin. The above-mentioned compounds can be used in a method of acting upon a CCK and/or gastrin receptor which comprises administering a therapeutically effective but non-toxic amount of such compound to an animal, preferably a human. A pharmaceutical composition comprising a pharmaceutically acceptable carrier and, dispersed therein, an effective but non-toxic amount of such compound is another aspect of this invention.

DETAILED DESCRIPTION OF THE INVENTION

Benzodiazepine analogs of Formula I provide antagonists of CCK and gastrin. The present invention further provides novel CCK and gastrin antagonist compound which are water soluble. The Benzodiazepine analogs of Formula I are useful in a method of antagonizing the binding of CCK to CCK receptors or antagonizing the binding of gastrin to gastrin receptors. The novel Benzodiazepine analogs of the present invention are illustrated by compounds having the formula:

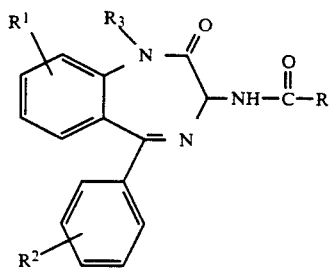

wherein: R is

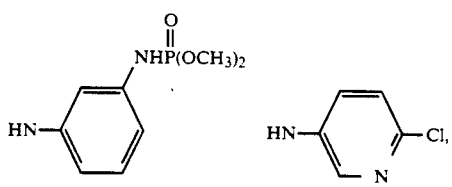

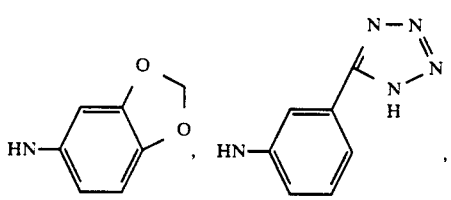

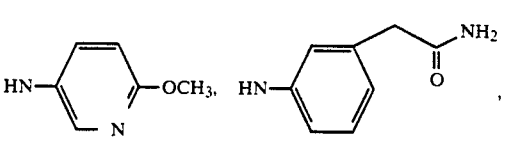

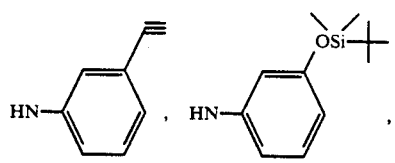

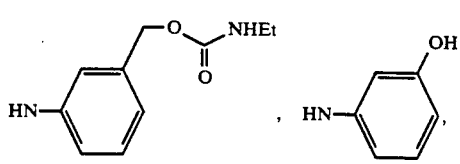

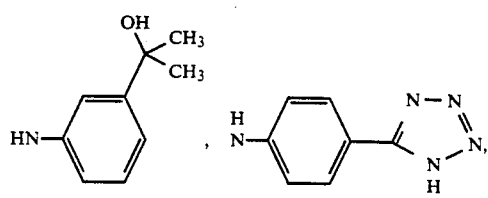

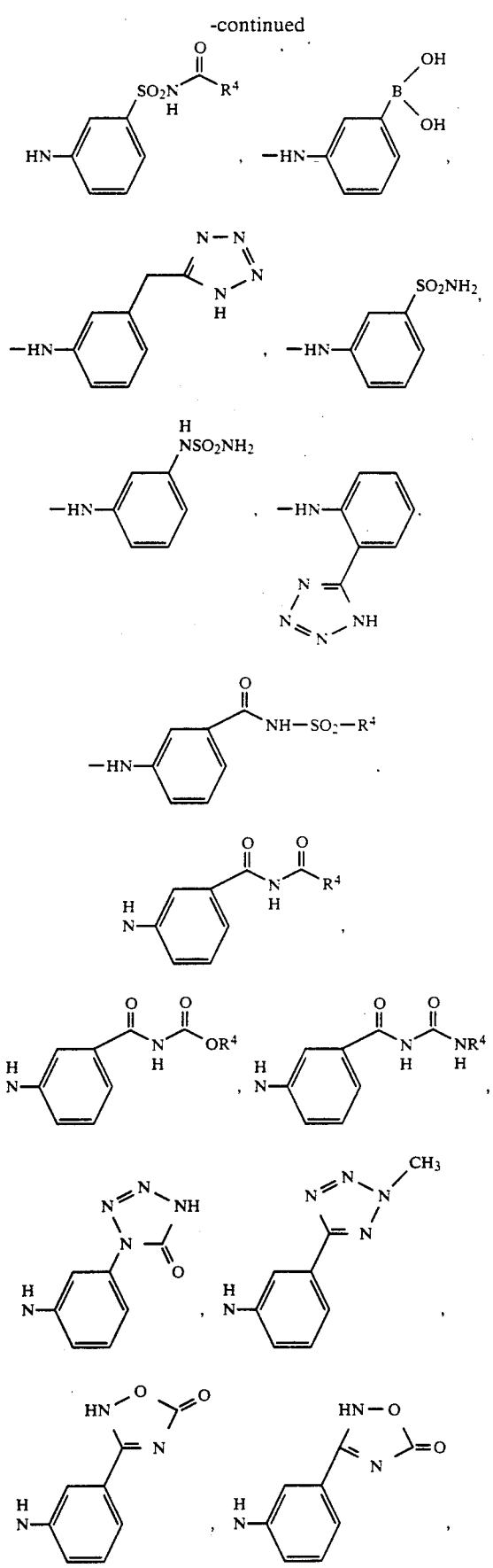

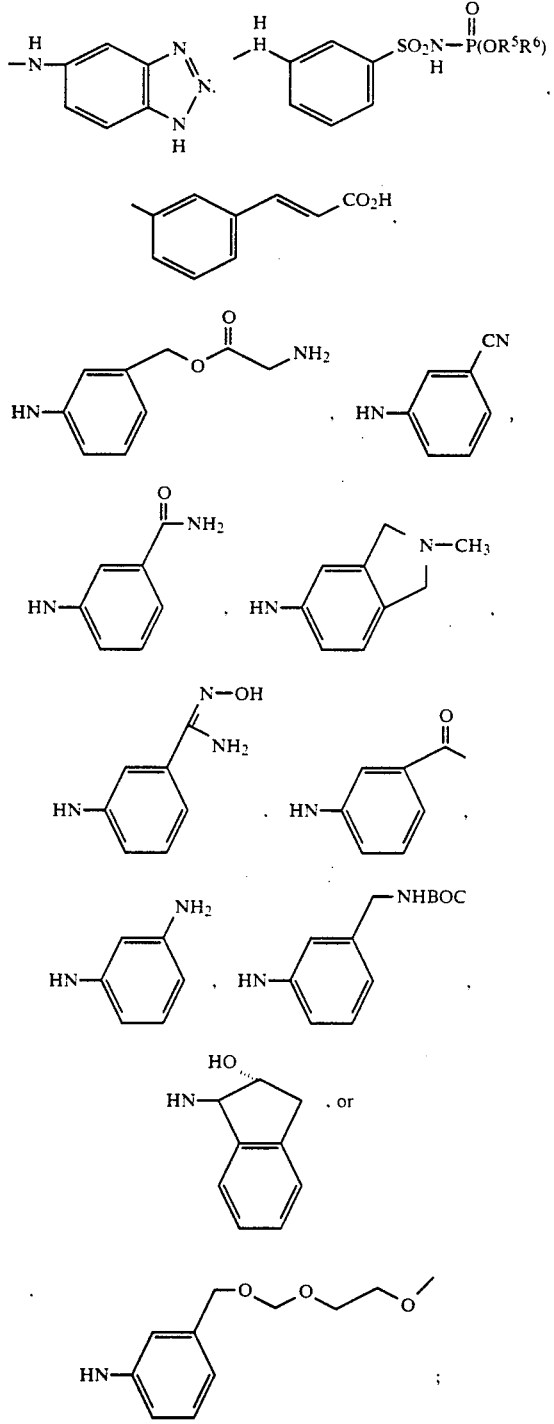

$R^1$ is absent, one or two of halogen or $CH_3$;
$R^2$ is absent, one or two of a halogen or $CH_3$;
$R^3$ is $C_1$-$C_6$ linear or branched chain alkyl or cyclopropylmethyl; and
$R^4$ is $C_1$-$C_6$ straight or branched chain alkyl, $CF_3$, cyclopropyl, 2,2-dimethylcyclopropyl, 2,2-difluorocyclopropyl, cyclobutyl, cyclopentyl, cyclohexyl, phenyl, or mono- or di-substituted phenyl wherein the substitution is F, Cl, Br, CN, $NO_2$, $CF_3$, $OCH_3$, or $NH_2$;
$R^5$ is H, methyl, ethyl, or phenyl;
$R^6$ is methyl, ethyl, or phenyl;
or the optical isomers, prodrugs or pharmaceutically acceptable salts thereof.

The preferred compounds of this invention as set forth in the Examples are as follows:
1. N-{1,3-Dihydro-1-methyl-2-oxo-5-phenyl-1H-1,4-benzodiazepin-3-yl}-N'-{[3-(1H-tetrazol-5-yl)phenyl]urea},
2. N-{1,3-Dihydro-1-[2-methyl]propyl-2-oxo-5-phenyl-1H-1,4-benzodiazepin-3-yl}-N'-{[3-(1H-tetrazol-5-yl)phenyl]urea},
3. N-{1,3-Dihydro-1-ethyl-2-oxo-5-phenyl-1H-1,4-benzodiazepin-3-yl}-N'-{[3-(1H-tetrazol-5-yl)phenyl]urea},
4. N-{1,3-Dihydro-1-[2-propyl]-2-oxo-5-phenyl-1H-1,4-benzodiazepin-3-yl}-N'-{[3-(1H-tetrazol-5-yl)phenyl]urea},
5. N-{1,3-Dihydro-1-methyl-2-oxo-5-phenyl-1H-1,4-benzodiazepin-3-yl}-N'-{[5-(2-chloro)pyridyl]urea},
6. N-{1,3-Dihydro-1-methyl-2-oxo-5-phenyl-1H-1,4-benzodiazepin-3-yl}-N'-{[5-(2-methoxy)pyridyl]urea},
7. N-{1,3-Dihydro-1-methyl-2-oxo-5-phenyl-1H-1,4-benzodiazepin-3-yl}-N'-{[3-(cyano)phenyl]urea},
8. N-{1,3-Dihydro-1-methyl-2-oxo-5-phenyl-1H-1,4-benzodiazepin-3-yl}-N'-{[3-(acetyl)phenyl]urea},
9. N-{1,3-Dihydro-1-methyl-2-oxo-5-phenyl-1H-1,4-benzodiazepin-3-yl}-N'-{[3-(amino)phenyl]urea},
10. N-{1,3-Dihydro-1-methyl-2-oxo-5-phenyl-1H-1,4-benzodiazepin-3-yl}-N'-{[3-(aminocarbonyl)phenyl]urea},
11. N-{1,3-Dihydro-1-methyl-2-oxo-5-phenyl-1H-1,4-benzodiazepin-3-yl}-N'-{[3-(dimethylphosphoramido), phenyl]urea},
12. N-{1,3-Dihydro-1-methyl-2-oxo-5-phenyl-1H-1,4-benzodiazepin-3-yl}-N'-{[3-(aminosulfonamido)-phenyl]urea},
13. N-{1,3-Dihydro-1-methyl-2-oxo-5-phenyl-1H-1,4-benzodiazepin-3-yl}-N'-{[benzotriazol-3-yl], urea},
14. N-{1,3-Dihydro-1-methyl-2-oxo-5-phenyl-1H-1,4-benzodiazepin-3-yl}-N'-{[3-(aminosulfonyl)phenyl]urea},
15. N-{1,3-Dihydro-1-methyl-2-oxo-5-phenyl-1H-1,4-benzodiazepin-3-yl}-N'-{[3-phenylboronyl]urea},
16. N-{1,3-Dihydro-1-methyl-2-oxo-5-phenyl-1H-1,4-benzodiazepin-3-yl}-N'-{[3-(acetylamino-sulfonyl)-phenyl]urea},
17. N-{1,3-Dihydro-1-methyl-2-oxo-5-phenyl-1H-1,4-benzodiazepin-3-yl}-N'-{[3-((1H-tetrazol-5-yl)methyl)phenyl]urea},
18. N-{1,3-Dihydro-1-n-propyl-2-oxo-5-phenyl-1H-1,4-benzodiazepin-3-yl}-N'-{[3-(1H-tetrazol-5-yl)phenyl]urea},
19. N-{1,3-Dihydro-1-(2-(S)-methylbutyl]-2-oxo-5-phenyl-1H-1,4-benzodiazepin-3-yl}-N'-{[3-(1H-tetrazol-5-yl)phenyl]urea},
20. N-{1,3-Dihydro-1-cyclopropylmethyl-2-oxo-5-phenyl-1H-1,4-benzodiazepin-3-yl}-N'-{[3-(1H-tetrazol-5-yl)phenyl]urea},
21. N-(3-(R,S)-2,3-Dihydro-5-(2-fluorophenyl)-1-(2-methylpropyl)-2-oxo-1H-1,4-benzodiazepin-3-yl]-N'-{[3-(tetrazol-5-yl)phenyl]urea},
22. N-{1,3-Dihydro-1-methyl-2-oxo-5-phenyl-1H-1,4-benzodiazepin-3-yl}-N'-{[3-(N-acetylcarboxamido)-phenyl]urea},
23. N-{1,3-Dihydro-1-methyl-2-oxo-5-phenyl-1H-1,4-benzodiazepin-3-yl}-N'-{[3-(N-(methanesulfonyl)carboxamido)phenyl]urea}, 24. N-{1,3-Dihydro-1-methyl-2-oxo-5-phenyl-1H-1,4-benzodiazepin-3-yl}-N'-{[3-(N-(2-propylsulfonyl)-carboxamido)phenyl]urea}, 25. N-{1,3-Dihydro-1-methyl-2-oxo-5-phenyl-1H-1,4-benzodiazepin-3-yl}-N'-{[3-(N-(t-butylsulfonyl)carboxamido)phenyl]urea}, 26. N-{1,3-Dihydro-1-methyl-2-oxo-5-phenyl-1H-1,4-benzodiazepin-3-yl}-N'-{[3-(N-(2-propylaminocarbonyl)carboxamido)phenyl]urea}, 27. N-{1,3-Dihydro-1-cyclopropylmethyl-2-oxo-5-phenyl-1H-1,4-benzodiazepin-3-yl}-N'-{[3-(N-(acetyl)-sulfonamido)phenyl]urea}, 28. N-{1,3-Dihydro-1-methyl-2-oxo-5-phenyl-1H-1,4-benzodiazepin-3-yl}-N'-{[3-(N-(1,1-dimethylethylcarbonyl)sulfonamido)phenyl]urea}, 29. N-{1,3-Dihydro-1-methyl-2-oxo-5-phenyl-1H-1,4-benzodiazepin-3-yl}-N'-{[3-(N-(2,2-dimethylcyclopropylcarbonyl)sulfonamido)phenyl]urea}, 30. N-{1,3-Dihydro-1-methyl-2-oxo-5-phenyl-1H-1,4-benzodiazepin-3-yl}-N'-{[3-(N-(t-butylaminocarbonyl)sulfonamido)phenyl]urea}, 31. N-{1,3-Dihydro-1-methyl-2-oxo-5-phenyl-1H-1,4-benzodiazepin-3-yl}-N'-{[3-(N-(diphenylphosphono)sulfonamido)phenyl]urea}, 32. N-{1,3-Dihydro-1-methyl-2-oxo-5-phenyl-1H-1,4-benzodiazepin-3-yl}-N'-{[3-(trans-carboxyethylene)-phenyl]urea}, 33. N-{1,3-Dihydro-1-methyl-2-oxo-5-phenyl-1H-1,4-benzodiazepin-3-yl}-N'-{[3-(2-methyltetrazol-5-yl)phenyl]urea}, 34. N-{1,3-Dihydro-1-methyl-2-oxo-5-phenyl-1H-1,4-benzodiazepin-3-yl}-N'-{[3-(1,2,4-oxadiazol-5-one)-phenyl]urea}, 35. N-{1,3-Dihydro-1-cyclopropylmethyl-2-oxo-5-phenyl-1H-1,4-benzodiazepin-3-yl}-N'-{[3-(1,2,4-oxadiazol-5-one)phenyl]urea}, 36. N-{1,3-Dihydro-1-methyl-2-oxo-5-phenyl-1H-1,4-benzodiazepin-3-yl}-N'-{[3-(1,2,4-oxadiathiazol-5-one)phenyl]urea}, 37. N-{1,3-Dihydro-1-methyl-2-oxo-5-phenyl-1H-1,4-benzodiazepin-3-yl}-N'-{[3-(1,3,4-triazol-5-one)-phenyl]urea}, or a pharmaceutically acceptable salt thereof.

The most preferred compounds of this invention as set forth in the Examples are as follows:

1. N-{1,3-Dihydro-1-methyl-2-oxo-5-phenyl-1H-1,4-benzodiazepin-3-yl}-N'-{[3-(1H-tetrazol-5-yl)phenyl]urea}, 2. N-{1,3-Dihydro-1-[2-methyl]propyl-2-oxo-5-phenyl-1H-1,4-benzodiazepin-3-yl}-N'-{[3-(1H-tetrazol-5-yl)phenyl]urea}, 18. N-{1,3-Dihydro-1-n-propyl-2-oxo-5-phenyl-1H-1,4-benzodiazepin-3-yl}-N'-{[3-(1H-tetrazol-5-yl)phenyl]urea}, 25. N-{1,3-Dihydro-1-methyl-2-oxo-5-phenyl-1H-1,4-benzodiazepin-3-yl}-N'-{[3-(N-(t-butyl-sulfonyl)carboxamido)phenyl]urea}, 34. N-{1,3-Dihydro-1-methyl-2-oxo-5-phenyl-1H-1,4-benzodiazepin-3-yl}-N'-{[3-(1,2,4-oxadizaol-5-one)-phenyl]urea}, or 35. N-{1,3-Dihydro-1-cyclopropylmethyl-2-oxo-5-phenyl-1H-1,4-benzodiazepin-3-yl}-N'-{[3-(1,2,4-oxadiazol-5-one)phenyl]urea}, or a pharmaceutically acceptable salt thereof.

It will be appreciated that formula (I) is intended to embrace all possible isomers, including optical isomers, and mixtures thereof, including racemates.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bungaard, Elsevier, 1985.

The pharmaceutically acceptable salts of the compounds of Formula I include the conventional non-toxic salts or the quarternary ammonium salts of the compounds of Formula I formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formula I are also readily prepared by conventional procedures such as treating an acid of Formula I with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammonium hydroxide and the like.

The compounds of Formula I antagonize CCK and/or gastrin and are useful as pharmaceutical agents for animals, preferably for mammals, and most especially for humans, for the treatment and prevention of gastrointestinal disorders and central nervous system disorders.

Examples of such gastrointestinal disorders include ulcers, such as peptic and gastrointestinal ulcers, irritable bowel syndrome, gastroesophagenal reflux disease or excess pancreatic or gastrin secretion, acute pancreatitis, or motility disorders, Zollinger-Ellison syndrome, and antral and cell hyperplasia.

Examples of central nervous system disorders include central nervous system disorders caused by CCK interaction with dopamine, such as neuroleptic induced tardive dyskinesia, Parkinson's disease, schizophrenia, other psychosis or Gilles de la Tourette syndrome, and disorders of appetite regulatory systems.

The compounds of Formula I may further be useful in the treatment or prevention of additional central nervous system disorders including neurological and psychiatric disorders. Examples of such central nervous system disorders include anxiety disorders and panic disorders, wherein CCK and/or gastrin is involved. Additional examples of central nervous system disorders include panic syndrome, anticipatory anxiety, phobic anxiety, panic anxiety, chronic anxiety, and endogeneous anxiety.

The compounds of Formula I may further be useful in the treatment of oncologic disorders wherein CCK or gastrin may be involved. Examples of such oncologic disorders include small cell adenocarcinomas and primary tumors of the central nervous system glial and neuronal cells. Examples of such adenocarcinomas and tumors include, but are not limited to, tumors of the lower esophagus, stomach, intestine, colon and lung, including small cell lung carcinoma.

The compounds of Formula I may further be used to control pupil constriction in the eye. The compounds may be used for therapeutic purposes during eye examinations and intraocular surgery in order to prevent miosis. The compounds may further be used to inhibit miosis occurring in association with iritis, uveitis and trauma.

The compounds of Formula I are also useful for directly inducing analgesia, opiate or non-opiate mediated, as well as anesthesia or loss of the sensation of pain.

The compounds of Formula I may further be useful for preventing or treating the withdrawal response produced by chronic treatment or abuse of drugs or alcohol. Such drugs include, but are not limited to, cocaine, alcohol or nicotine.

The compounds of Formula I are also useful for directly inducing analgesia, opiade or non-opiade mediated, as well as anesthesia or loss of the sensation of pain.

The compounds of formula (I) may also be useful as neuroprotective agents, for example, in the treatment and/or prevention of neurodegenerative disorders arising as a consequence of such pathological conditions as stroke, hypoglycaemia, cerebal palsy, transient cerebral ischaemic attack, cerebral ischaemia during cardiac pulmonary surgery or cardiac arrest, perinatal asphyxia, epilepsy, Huntington's chorea, Alzheimer's disease, Amyotrophic Lateral Sclerosis, Parkinson's disease, Olivo-pontocerebellar atrophy, anoxia such as from drowning, spinal cord and head injury, and poisoning by neurotoxins, including environmental neurotoxins.

The present invention also encompasses a pharmaceutical composition useful in the treatment of CCK and/or gastrin disorders comprising the administration of a therapeutically effective but non-toxic amount of the compounds of Formula I, with or without pharmaceutically acceptable carriers or diluents.

The compounds of Formula I, may be administered to animals, preferably to mammals, and most especially to a human subject either alone or, preferably, in combination with pharmaceutically-acceptable carriers or diluents, optionally with known adjuvants, such as alum, in a pharmaceutical composition, according to standard pharmaceutical practice. The compounds can be administered orally or parenterally, including intravenous, intramuscular, intraperitoneal, subcutaneous and topical administration.

For oral use of an antagonist of CCK, according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

When a compound according to Formula I is used as an antagonist of CCK or gastrin in a human subject, the daily dosage will normally be determined by the prescribing physician with the dosage generally varying according to the age, weight, and response of the individual patient, as well as the severity of the patient's symptoms. However, in most instances, an effective daily dosage will be in the range of from about 0.005 mg/kg to about 50 mg/kg of body weight, and preferably, of from about 0.05 mg/kg to about 50 mg/kg of body weight, and most preferably, of from about 0.5 mg/kg to about 20 mg/kg of body weight, administered in single or divided doses.

In some cases, however, it may be necessary to use dosage levels outside these limits. For example, doses as low as about 1 ng/kg, about 0.005 $\mu$g to about 0.05 $\mu$g, or about 100 ng to about 100 $\mu$g/kg may be administered.

In the effective treatment of panic syndrome, panic disorder, anxiety disorder and the like, preferably about 0.05 mg/kg to about 1.0 mg/kg of CCK antagonist may be administered orally (p.o.), administered in single or divided doses per day (b.i.d.). Other routes of administration are also suitable.

For directly inducing analgesia, anesthesia or loss of pain sensation, the effective dosage range is preferably from about 100 ng/kg to about 1 mg/kg by intraperitoneal administration. Oral administration is an alternative route, as well as others.

In the treatment of irritable bowel syndrome, preferably about 0.1 to 10 mg/kg of CCK antagonist is administered orally (p.o.), administered in single or divided doses per day (b.i.d.). Other routes of administration are also suitable.

The use of a gastrin antagonist as a tumor palliative for gastrointestinal neoplasma with gastrin receptors, as a modulator of central nervous activity, treatment of Zollinger-Ellison syndrome, or in the treatment of peptic ulcer disease, an effective dosage is preferably from about 0.1 to about 10 mg/kg, administered one-to-four times daily is indicated.

Because these compounds antagonize the function of CCK in animals, they may also be used as feed additives to increase the food intake of animals in daily dosage preferably from about 0.05 mg/kg to about 50 mg/kg of body weight.

The compounds of Formula I may be prepared according to the reaction schemes as set forth below.

SCHEME 1
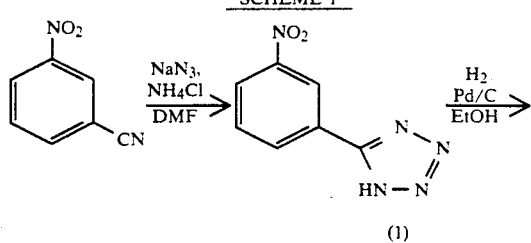
(1)
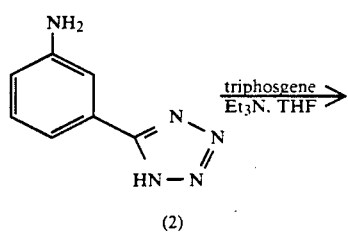
(2)
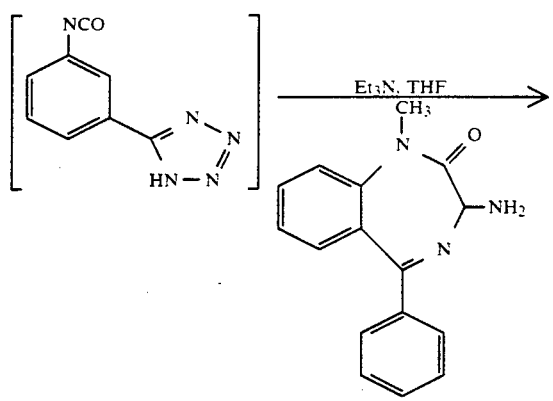
(3)
SCHEME 2
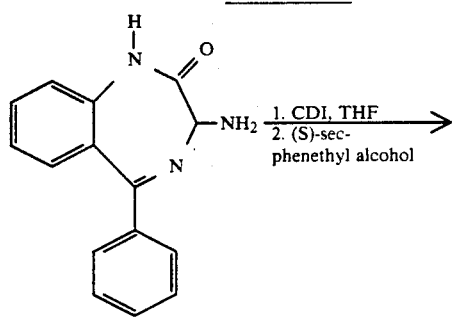
-continued
SCHEME 2
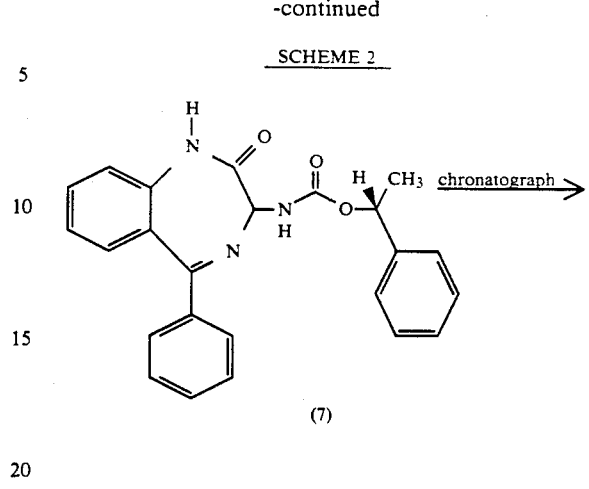
(7)
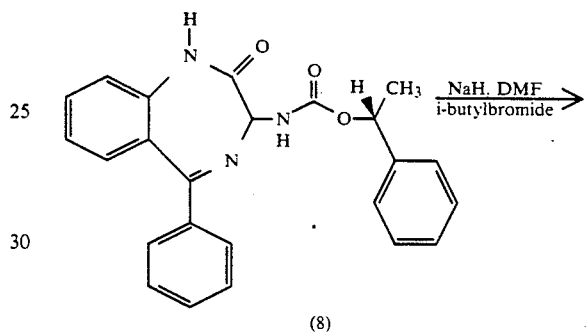
(8)
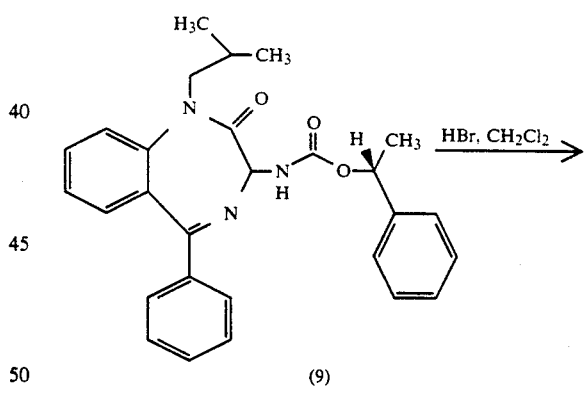
(9)
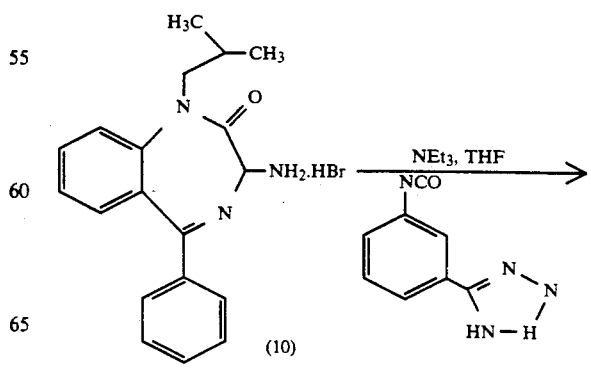
(10)

-continued
SCHEME 2
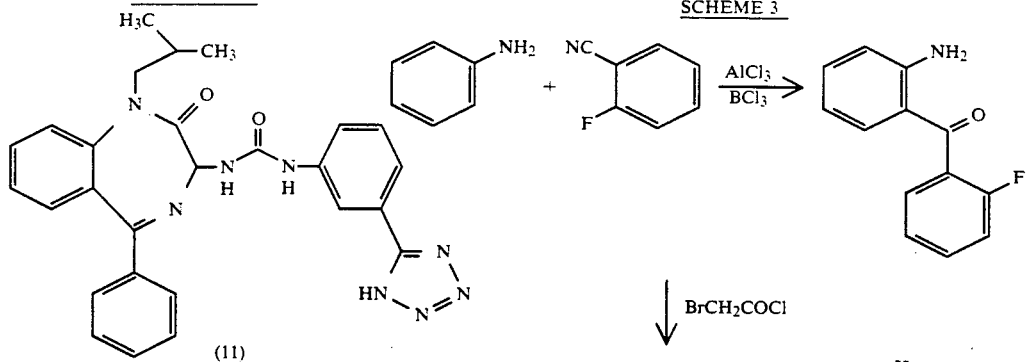
(11)
SCHEME 3
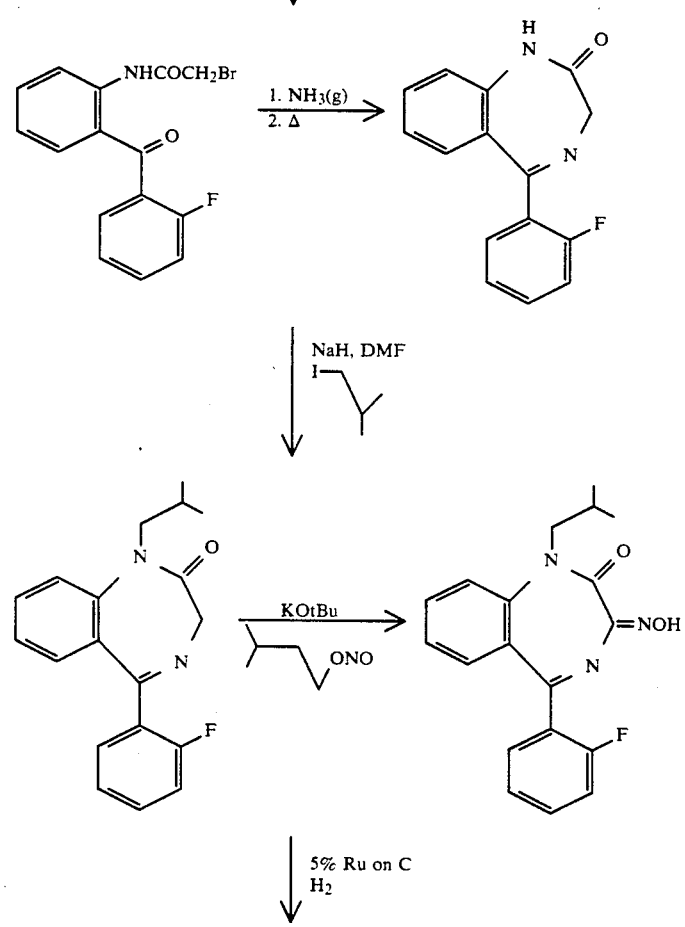

SCHEME 3

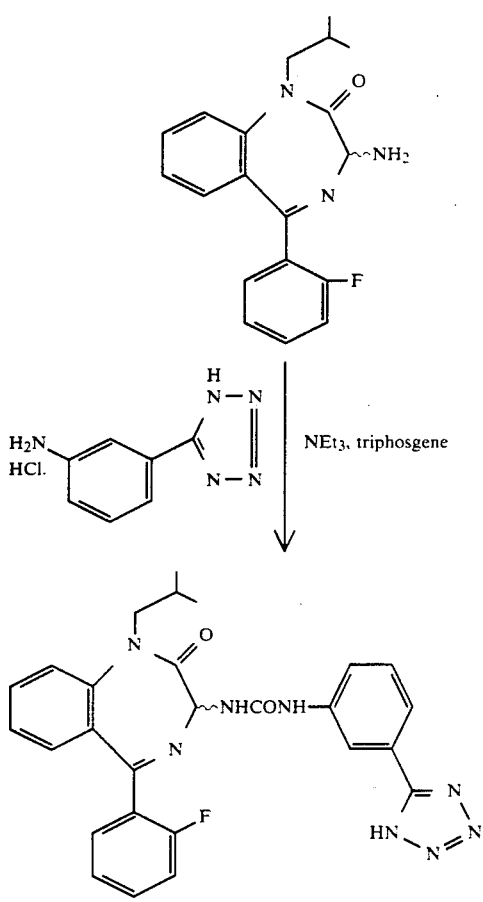

1. CCK Receptor Binding (Pancreas)

CCK-8 sulphated was radiolabelled with $^{125}$I-Bolton Hunter reagent (2000 Ci/mmole). Receptor binding was performed according to Chang and Lotti (Proc. Natl. Acad. Sci. 83, 4923–4926, 1986) with minor modifications.

Male Sprague-Dawley rats (150–200 g) were sacrificed by decapitation. The whole pancreas was dissected free of fat tissue and was homogenized in 25 volumes of ice-cold 10 mM Hepes buffer with 0.1% soya bean trypsin inhibitor (pH 7.4 at 25° C.) with a Kinematica Polytron. The homogenates were centrifuged at 47,800 g for 10 min. Pellets were resuspended in 10 volumes of binding assay buffer (20 mM Hepes, 1 mM EGTA, 5 mM MgCl$_2$, 150 mM NaCl, bacitracin 0.25 mg/ml, soya bean trypsin inhibitor 0.1 mg/ml, and bovine serum albumin 2 mg/ml, pH 6.5 at 25° C.) using a teflon homogenizer, 15 strokes at 500 rpm. The homogenate was further diluted in binding assay buffer to give a final concentration of 0.5 mg original wet weight/1 ml buffer. For the binding assay, 50 μl of buffer (for total binding) or unlabeled CCK-8 sulfated to give a final concentration of 1 μM (for nonspecific binding) or the compounds of Formula I (for determination of inhibition of $^{125}$I-CCK binding) and 50 μl of 500 pM $^{125}$I-CCK-8 (i.e. 50 pM final concentration) were added to 400 μl of the membrane suspensions in microfuge tubes. All assays were run in duplicate. The reaction mixtures were incubated at 25° C. for 2 hours and the reaction terminated by rapid filtration (Brandell 24 well cell harvester) over Whatman GF/C filters, washing 3×4 mls with ice-cold 100 mM NaCl. The radioactivity on the filters was counted with a LKB gamma counter.

2. CCK Receptor Binding (Brain)

CCK-8 sulphated was radiolabelled and the binding was performed according to the description for the pancreas method with minor modifications.

Male Hartley guinea pigs (300–500 g) were sacrificed by decapitation and the cortex was removed and homogenized in 25 mL ice-cold 0.32M sucrose. The homogenates were centrifuged at 1000 g for 10 minutes and the resulting supernatant was recentrifuged at 20,000 g for 20 minutes. The P$_2$ pellet was resuspended in binding assay buffer (20 mM N-2-hydroxyethyl-piperazine-N'-2-ethane sulfonic acid (HEPES), 5 mM MgCl$_2$, 0.25 mg/ml bacitracin, 1 mM ethylene glycol-bis-(β-aminoethylether-N,N'-tetraacetic acid) (EGTA) pH 6.5 at 25° C., using a teflon homogenizer (5 strokes at 500 rpm) to give a final concentration of 10 mg original wet weight 11.2 mls buffer. For the binding assay, 50 μl of buffer (for total binding) or unlabeled CCK-8 sulfate to give a final concentration of 1 μM (for nonspecific binding) or the compounds of Formula I (for determination of inhibition of $^{125}$I-CCK-8 binding) and 50 μl of 500 pM $^{125}$I-CCK-8 (i.e. final concentration of 50 pM) were added to 400 μl of the membrane suspensions in microfuge tubes. All assays were run in duplicate. The reaction mixtures were incubated at 25° C. for 2 hours and then the reaction was terminated on Whatman GF/C filters by rapid filtration (Brandell 24 well cell Harvester) with 3×5 ml washes of cold 100 mM NaCl. The radioactivity on the filters was then counted with a LKB gamma counter.

5. Gastrin Antagonism

Gastrin antagonist activity of compounds of Formula I is determined using the following assay.

A. Gastrin Receptor Binding in Guinea Pig Gastric Glands

Preparation of guinea pig gastric mucosal glands

Guinea pig gastric mucosal glands were prepared by the procedure of Chang et al., Science 230, 177-179 (1985) with slight modification. Gastric mucosa from guinea pigs (300-500 g body weight, male Hartley) were isolated by scraping with a glass slide after washing stomachs in ice-cold, aerated buffer consisting of the following: 130 mM NaCl, 12 mM $NaHCO_3$, 3 mM $NaH_2PO_4$, 3 mM $Na_2HPO_4$, 3 mM $K_2HPO_4$, 2 mM $MgSO_4$, 1 mM $CaCl_2$, 5 mM glucose and 4 mM L-glutamine, 50 mM HEPES, 0.25 mg/ml bacitracin, 0.10 mg/ml soya bean trypsin inhibitor, 0.1 mg/ml bovine serum albumin, at pH 6.5, and then incubated in a 37° C. shaking water bath for 40 minutes in buffer containing 1 mg/ml collagenase and bubbled with 95% $O_2$ and 5% $CO_2$. The tissues were passed twice through a 5 ml syringe to liberate the gastric glands, and then filtered through Nitex #202 gauge nylon mesh. The filtered glands were centrifuged at 272 g for 5 minutes and washed twice by resuspension in 25 ml buffer and centrifugation.

B. Binding studies

The washed guinea pig gastric glands prepared as above were resuspended in 25 ml of standard buffer. For binding studies, to 250 μl of gastric glands, 30 μl of buffer (for total binding) or gastrin (3 μM final concentration, for nonspecific binding) or test compound and 20 μl of $^{125}$I-gastrin (NEN, 2200 Ci/mmole, 0.1 nM final concentration) were added. AV assays were run in triplicate. The tubes were aerated with 95% $O_2$ and 5% $CO_2$ and capped. The reaction mixtures after incubation at 25° C. for 30 minutes in a shaking water bath were rapidly filtered (Brandell 24 well cell harvester) over Whatman and G/F B filters presoaked in assay buffer and immediately washed further with 3×4 ml of 100 mM ice cold NaCl. The radioactivity on the filters was measured using a LKB gamma counter.

In Vitro Results

Effect of the Compounds of Formula I on $^{125}$I-CCK-8 receptor binding

The preferred compounds of Formula I are those which produced dose-dependent inhibition of specific $^{125}$I-CCK-8 binding as defined as the difference between total and non-specific (i.e. in the presence of 1 μm CCK) binding.

Drug displacement studies were performed with at least 10 concentrations of compounds of formula 1 and the $IC_{50}$ values were determined by regression analysis. $IC_{50}$ refers to the concentration of the compound required to inhibit 50% of specific binding of $^{125}$I-CCK-8.

The data in Table I were obtained for compounds of Formula I.

TABLE I

| CCK RECEPTOR BINDING RESULTS $IC_{50}$ (μM) | | | |
|---|---|---|---|
| Compound Example | $^{125}$I-CCK Pancreas | $^{125}$I-CCK Brain | $^{125}$I-CCK Gastric Glands |
| 1. | 0.400 | 0.001 | 0.0007 |

TABLE I-continued

| CCK RECEPTOR BINDING RESULTS $IC_{50}$ (μM) | | | |
|---|---|---|---|
| Compound Example | $^{125}$I-CCK Pancreas | $^{125}$I-CCK Brain | $^{125}$I-CCK Gastric Glands |
| 2. | 1.4 | 0.0001 | 0.00024 |
| 3. | 0.029 | 0.0016 | N.D. |
| 4. | 0.2 | 0.0041 | N.D. |
| 5. | >3 | 0.046 | N.D. |
| 6. | 2 | 0.048 | N.D. |
| 7. | 3.1 | 0.027 | N.D. |
| 8. | 1.2 | 0.0036 | N.D. |
| 9. | >3 | 0.033 | N.D. |
| 10. | 1.36 | 0.028 | N.D. |
| 11. | 0.3 | 0.1 | N.D. |
| 12. | 0.53 | 0.032 | N.D. |
| 13. | 1.5 | 0.019 | N.D. |
| 14. | 4.4 | 0.074 | N.D. |
| 15. | 0.42 | 0.0096 | N.D. |
| 16. | >3 | 0.0039 | N.D. |
| 17. | 1.8 | 0.0048 | N.D. |
| 18. | 1.1 | 0.000067 | N.D. |
| 19. | 0.5 | 0.00025 | N.D. |
| 20. | 870 | 0.0004 | N.D. |
| 21. | 0.15 | 0.0014 | N.D. |
| 22. | 3.8 | 0.055 | N.D. |
| 23. | 1.5 | 0.012 | N.D. |
| 24. | 2.4 | 0.0076 | N.D. |
| 25. | >3 | 0.00038 | N.D. |
| 26. | >3 | 0.41 | N.D. |
| 27. | 4.6 | 0.00055 | N.D. |
| 28. | >3 | 0.012 | N.D. |
| 29. | >3 | 0.011 | N.D. |
| 30. | >3 | 0.014 | N.D. |
| 31. | >3 | 0.015 | N.D. |
| 32. | 0.012 | 0.0089 | N.D. |
| 33. | 1.6 | 0.021 | N.D. |
| 34. | 1.1 | 0.00019 | N.D. |
| 35. | 0.19 | 0.00009 | N.D. |
| 36. | 1.52 | 0.0196 | N.D. |
| 37. | 2.46 | 0.00362 | N.D. |

(N.D. = No Data)

EXAMPLES

Examples provided are intended to assist in a further understanding of the invention. Particular materials employed, species, and conditions are intended to be further illustrative of the invention and not limitative of the reasonable scope thereof.

EXAMPLE 1

Synthesis of N-{1,3-Dihydro-1-methyl-2-oxo-5-phenyl-1H-1,4-benzodiazepin-3-yl}N'-{[3-(1H-tetrazol-5-yl)phenyl]urea A) 3-Nitro-(1H-tetrazol-5-yl)benzene (1)

Nitrobenzonitrile (5 g) was dissolved in 50 ml of dry N,N-dimethylformamide and mixed with 10.97 g of sodium azide and 9.03 g ammonium chloride. The resulting suspension was heated to 110° C. for 18 hours. The reaction mixture was concentrated in vacuo and the residue was dissolved in water (50 ml). The aqueous solution was washed with ethyl acetate and acidified with 1 N HCl solution. The aqueous phase was then extracted with ethyl acetate and the organic extracts were dried (sodium sulfate) and concentrated to give 8.5 g of the title compound as a white solid.

B) 3-Amino-(1H-tetrazol-5-yl)benzene (2)

3-Nitro-(1H-tetrazol-5-yl)benzene was dissolved in 200 ml of ethanol, treated with 1.7 g of 10% palladium/carbon catalyst, and hydrogenated on a Parr apparatus at 30 psi for 2 hours. The reaction mixture was filtered through Celite and concentrated to give 4.7 g of the title compound.

C) N-{1,3-Dihydro-1-methyl-2-oxo-5-phenyl-1H-1,4-benzodiazepin-3-yl}-N'-{[3-(1H-tetrazol-5-yl)phenyl]urea}. (3)

A solution of 346 mg of 3-amino-(1H-tetrazol-5-yl)benzene in 20 ml of tetrahydrofuran was stirred magnetically in an ice bath and treated in sequence with triethylamine (314 μL) and triphosgene (224 mg) under anhydrous conditions. The pH of the reaction mixture was adjusted to 8 by the addition of triethylamine. After 15 minutes, 400 mg of 3-(R)-amino-1,3-dihydro-1-methyl-5-phenyl-2H-1,4-benzodiazepin-2-one was added and the reaction mixture was stirred at room temperature overnight. The reaction mixture was concentrated under reduced pressure and the residue was partitioned between ethyl acetate and 25% acetic acid solution. The aqueous layer was extracted with ethyl acetate and the combined organic extracts were dried (sodium sulfate) and roto-evaporated. Flash column chromatography of the crude reaction product on silica gel (chloroform-methanolacetic acid, 95:5:0.5, v/v elution) afforded 260 mg of the title compound: m.p. 180° C. (d).

HPLC=98% pure at 214 nm; TLC $R_f$=0.16 (CHCl$_3$—CH$_3$OH, 9:1).

NMR (DMSO-D$_6$): Consistent with structure assignment and confirms presence of solvent.

FAB MS: 453 (M$^+$ +1).

Analysis for C$_{24}$H$_{20}$N$_8$O$_2$.0.30 CHCl$_3$.1.2 CH$_3$OH: Calculated: C, 58.14; H, 4.80; N, 21,27. Found: C, 58.19; H, 4.68; N, 21.09.

EXAMPLE 2

Synthesis of
N-{1,3-Dihydro-1-[2-methyl]propyl-2-oxo-5-phenyl-1H-1,4,-benzodiazepin-3-yl}-N'-{[3-(1H-tetrazol-5-yl)phenyl]urea}

(A) 1,3-Dihydro-5-phenyl-3-(R)-{[(α-methyl)benzyloxycarbonyl]-amino}-2H-1,4-benzodiazepin-2-one and 1,3-Dihydro-5-phenyl-3-(S)-{[(α-methyl)benzyloxycarbonyl]-amino}-2H-1,4-benzodiazepin-2-one. (7)

1,3-Dihydro-5-phenyl-3(R,S)-amino-2H-1,4-benzodiazepin-2-one (647 mg) and 459 mg of carbonyldiimidazole were combined in 20 ml of dry tetrahydrofuran. The resulting solution was protected from moisture and stirred for 20 hours at room temperature. To this solution was then added 360 μL of (S)-(−)-sec-phenethyl alcohol and the reaction mixture was heated to the refluxing temperature of the solvent for 2.5 hours. Additional amounts of (S)-(−)-sec-phenethyl alcohol were added in increments throughout the course of the reaction until a total of 1.06 ml had been added. After refluxing for 75 hours the reaction was complete. The reaction mixture was cooled and concentrated. The residual material was applied to a silica gel column (13 cm×60 mm) and the diastereomeric mixture was separated by eluting with the following gradients: 28% ethyl acetate in hexane (1L), 33% ethyl acetate in hexane (1L). 35% ethyl acetate in hexane (1L), 40% ethyl acetate in hexane (1L). In this way, 170 mg of the less polar 3-(R) (8) and 100 mg of the more polar 3-(S) diastereomer were obtained. (The remaining mass balance was collected as a mixture of diastereomers).

(B) 1,3-Dihydro-1-(2-methyl)propyl-3-(R)-{[(α-methyl)benzyloxycarbonyl]-amino}-5-phenyl-2H-1,4-benzodiazepin-2-one. (9)

1,3-Dihydro-5-phenyl-3-(R)-}[(α-methyl)benzyloxycarbonyl]-amino}-2H-1,4-benzodiazepin-2-one (155 mg) in 4 ml of dry N,N-dimethylformamide was stirred magnetically in an ice bath under an inert atmosphere. Sodium hydride (18 mg, 60% oil dispersion) was added and the reaction mixture was stirred at 0° C. After 1 hour 51 μL of isobutylbromide was added and the reaction mixture was warmed to room temperature over 1.75 hours. Two more portions of isobutylbromide (35 μL) were added over 4 hours and 5 mg of sodium hydride was added. The reaction mixture was stirred for 28 hours, concentrated in vacuo, and the residue was chromatographed on five 1 mm×20 cm×20 cm precoated silica gel plates (9:1 chloroform-methanol elulution) to give 68 mg of the desired product.

(C) 1,3-Dihydro-1-(2-methyl)propyl-3-(R)-amino-5-phenyl-2H-1,4-benzodiazepin-2-one hydrobromide. (10)

1,3-Dihydro-1-(2-methyl)propyl-3-(R)-{[(α-methyl)-benzyloxycarbonyl]-amino}-5-phenyl-2H-1,4-benzodiazepin-2-one (68 mg) was dissolved in 8 ml of dry methylene chloride. The solution was cooled to 0° C. and saturated with hydrogen bromide gas. After 30 minutes the solvent and excess hydrogen bromide were removed under reduced pressure to give 67 mg of a pale yellow powder.

(D) N-{3-(R)-1,3-Dihydro-1-(2-methyl)propyl-2-oxo-5-phenyl-1H-1,4-benzodiazepin-3-yl}-N'-{[3-(1H-tetrazol-5-yl)phenyl]urea}. (11)

A solution of 27.3 mg of 3-amino-(1H-tetrazol-5-yl)benzene in 2 ml of tetrahydrofuran was stirred magnetically in an ice bath and treated in sequence with triethylamine (18.1 μL) and triphosgene (16.6 mg) under anhydrous conditions. The pH of the reaction mixture was adjusted to approximately 8 with the incremental addition of triethylamine. After 15 minutes, 40 mg of 3-(R)-amino-1,3-dihydro-1-methyl-5-phenyl-2H-1,4-benzodiazepin-2-one was added and the reaction mixture was stirred at room temperature for 15 minutes more. The reaction mixture was concentrated under reduced pressure and the residue was partitioned between ethyl acetate and 25% acetic acid solution. The aqueous layer was extracted with ethyl acetate and the combined organic extracts were dried (sodium sulfate) and roto-evaporated. Preparative thick layer chromatography of the crude reaction product on two 1 mm×20 cm×20 cm precoated silica gel plates (chloroform-methanol-acetic acid, 92:8:0.8, v/v elution) afforded the title compound: m.p.>200° C. (d).

HPLC=>99% pure at 214 nm; TLC $R_f$=0.48 (CHCl$_3$—CH$_3$OH—HOAc 90:10:1, v/v).

NMR (DMSO-D$_6$): Consistent with structure assignment and confirms presence of solvent.

FAB MS: 495 (M$^+$ +1).

Analysis for C$_{27}$H$_{26}$N$_8$O$_2$.0.9 CH$_3$OH: Calculated: C, 60.56; H, 5.39; N, 20.04. Found: C, 60.56; H, 5.01; N, 19.91.

EXAMPLE 3

Synthesis of
N-{1,3-Dihydro-1-ethyl-2-oxo-5-phenyl-1H-1,4-benzodiazepin-3-yl}-N'-{[3-(1H-tetrazol-5-yl)phenyl]urea}

A solution of 90.2 mg of 3-amino-(1H-tetrazole-5-yl)benzene in 2 ml of tetrahydrofuran was stirred magnetically in an ice bath and treated in sequence with triethylamine (78 μL) and triphosgene (55 mg) under anhydrous conditions. The pH of the reaction mixture was adjusted to 8 by the addition of an additional 78 μL triethylamine. After 30 minutes, 190 mg of 3-amino-1,3-dihydro-1-ethyl-5-phenyl-2H-1,4-benzodiazepin-2-one was added and the reaction mixture was stirred at room temperature for 30 minutes more. The reaction mixture was concentrated under reduced pressure and the residue was partitioned between ethyl acetate and 25% acetic acid solution. The aqueous layer was extracted with ethyl acetate and the combined organic extracts were dried (sodium sulfate) and roto-evaporated. Preparative thick layer chromatography of the crude reaction product on silica gel (chloroform-methanol-acetic acid, 90:10:0.1, v/v elution) afforded the title compound: m.p. 200° C. (shrinks).

HPLC=>98% pure at 214 nm; TLC $R_f$=0.40 (CHCl$_3$—CH$_3$OH—HOAc, 90:10:1).

NMR(DMSO-D$_6$): Consistent with structure assignment and confirms presence of solvent.

FAB MS: 467 (M+ +1).

Analysis for C$_{25}$H$_{22}$N$_8$O$_2$.0.9 CH$_3$OH: Calculated: C, 62.80; H, 5.21; N, 22.62. Found: C, 62.85; H, 4.92; N, 22.43.

EXAMPLE 4

Synthesis of
N-{1,3-Dihydro-1-[2-propyl]-2-oxo-5-phenyl-1H-1,4-benzodiazepin-3-yl}-N'-{[3-(1H-tetrazol-5-yl)phenyl]urea}

By employing reaction conditions identical to those described in Example 3, except that 3-amino-1,3-dihydro-1-[2-propyl]-5-phenyl-2H-1,4-benzodiazepin-2-one was substituted for 3-amino-1,3-dihydro-1-ethyl-5-phenyl-2H-1,4-benzodiazepin-2-one, the title compound was obtained as a white solid: m.p. 200° C. (d);

HPLC=>97% pure at 214 nm; TLC $R_f$=0.33 (CHCl$_3$—CH$_3$OH—HOAc, 90:10:1).

NMR(DMSO-D$_6$): Consistent with structure assignment and confirms presence of solvent.

FAB MS: 481 (M+ +1).

Analysis for C$_{26}$H$_{24}$N$_8$O$_2$.0.6 HOAc.0.2 H$_2$O: Calculated: C, 62.80; H, 5.19; N, 21.54. Found: C, 62.75; H, 5.27; N, 21.54.

EXAMPLE 5

N-{1,3-Dihydro-1-methyl-2-oxo-5-phenyl-1H-1,4-benzodiazepin-3-yl}-N'-{[5-(2-chloro)pyridyl]urea}

A solution of 97 mg of 5-amino-2-chloropyridine in 2 ml of tetrahydrofuran was stirred magnetically in an ice bath and treated in sequence with triethylamine (105 µL) and triphosgene (75 mg) under anhydrous conditions. After 20 minutes, 200 mg of 3-(R)-amino-1,3-dihydro-1-methyl-5-phenyl-2H-1,4-benzodiazepin-2-one was added and the pH of the reaction mixture adjusted to 8 by the addition of an additional 105 µL of triethylamine. The reaction mixture was stirred at room temperature for 2 hours and then was concentrated under reduced pressure. The residue was partitioned between ethyl acetate and water. The aqueous layer was extracted with ethyl acetate and the combined organic extracts were dried (sodium sulfate) and roto-evaporated. The crude product was recrystallized from an ethyl acetate-hexane solvent mixture to give 190 mg of the title compound: m.p.>190° C. (d).

HPLC=99% pure at 214 nm; TLC $R_f$=0.55 (CH$_2$Cl$_2$—CH$_3$OH, 9:1).

NMR(DMSO-D$_6$): Consistent with structure assignment and confirms presence of solvent.

FAB MS: 420 (M+ +1).

Analysis for C$_{22}$H$_{18}$ClN$_5$O$_2$.0.15 EtOAc.0.35 H$_2$O: Calculated: C, 61.77; H, 4.57; N, 15,94. Found: C, 61.74; H, 4.39; N, 15.97.

EXAMPLE 6

N-{1,3-Dihydro-1-methyl-2-oxo-5-phenyl-1H-1,4-benzodiazepin-3-yl}-N'-{[5-(2-methoxy)pyridyl]urea}

By employing reaction conditions identical to those described in Example 5, except that 5-amino-2-methoxypyridine was substituted for 5-amino-2-chloropyridine, the title compound was obtained as a white solid after purification by preparative thick layer chromatography on silica gel (chloroform-methanol, 9:1): m.p. 168°-170° C.;

HPLC=98% pure at 214 nm; TLC $R_f$=0.48 (EtOAc).

NMR(DMSO-D$_6$): Consistent with structure assignment and confirms presence of solvent.

FAB MS: 416 (M+ +1).

Analysis for C$_{23}$H$_{21}$N$_5$O$_3$.0.25 EtOAc.0.35 H$_2$O: Calculated: C, 64.95; H, 5.38; N, 15.78. Found: C, 64.91; H, 5.23; N, 15.71.

EXAMPLE 7

N-{1,3-Dihydro-1-methyl-2-oxo-5-phenyl-1H-1,4-benzodiazepin-3-yl}-N'-{[3-(cyano)phenyl]urea}

A solution of 891 mg of 3-aminobenzonitrile in 20 ml of methylene chloride was stirred magnetically in an ice bath and treated in sequence with triethylamine (525 µL) and triphosgene (745 mg) under anhydrous conditions. The pH of the reaction mixture was adjusted to 8 by the addition of the requisite amount of triethylamine. After 15 minutes, 1 g of 3-(R)-amino-1,3-dihydro-1-methyl-5-phenyl-2H-1,4-benzodiazepin-2-one was added and the reaction mixture was stirred at room temperature for 15 minutes. The reaction mixture was diluted with methylene chloride and washed with saturated sodium sulfate solution, 1% HCl solution and brine, then dried (sodium sulfate) and concentrated under reduced pressure. The residue was recrystallized from a methanol-ethyl acetate solvent mixture to give 1.33 g of the title compound: m.p. 249°-250° C.

HPLC=>98% pure at 214 nm; TLC $R_f$=0.25 (Hexane-ethyl acetate, 1:1).

NMR(DMSO-D$_6$): Consistent with structure assignment and confirms presence of solvent.

FAB MS: 410 (M+ +1).

Analysis for C$_{24}$H$_{19}$N$_5$O$_2$.0.25 H$_2$O: Calculated: C, 69.63; H, 4.75; N, 16.92. Found: C, 69.68; H, 4.63; N, 17.06.

EXAMPLE 8

N-{1,3-Dihydro-1-methyl-2-oxo-5-phenyl-1H-1,4-benzodiazepin-3-yl}-N'-{[3-(acetyl)phenyl]urea}

3-(R)-Amino-1,3-dihydro-1-methyl-5-phenyl-2H-1,4-benzodiazepin-2-one (500 mg, 1.88 mmole) was dissolved in 5 ml of tetrahydrofuran and treated with 3-acetylphenylisocyanate (304 mg, 1.88 mmole) at room temperature. The reaction mixture was stirred for 1 hour and the resulting solid was collected. This crude product was recrystallized from chloroform to give 710 mg of the analytical material:

m.p. 225°-226° C.

HPLC=>99% pure at 214 nm; TLC $R_f$=0.21 (CHCl$_3$—CH$_3$OH, 95:5).

NMR(DMSO-D$_6$): Consistent with structure assignment and confirms presence of solvent.

FAB MS: 427 (M+ +1).

Analysis for $C_{25}H_{22}N_4O_3 \cdot 0.35 H_2O$: Calculated: C, 69.38; H, 5.29; N, 12.95. Found: C, 69.36; H, 5.13; N, 13.06.

EXAMPLE 9

N-{1,3-Dihydro-1-methyl-2-oxo-5-phenyl-1H-1,4-benzodiazepin-3-yl}-N'-{[3-(amino)phenyl]urea}

To 640 mg (1.49 mmole) of the carbamate resulting from the addition of 4-nitrophenylchloroformate to 3-(R)-amino-1,3-dihydro-1-methyl-5-phenyl-2H-1,4-benzodiazepin-2-one in 20 ml of N,N-dimethylformamide was added triethylamine (228 µL) at room temperature. 1,3-Phenylenediamine (806 mg) was added and the resulting mixture was heated at 40° C. for 2 hours. The reaction mixture was concentrated and the residue was partitioned between ethyl acetate and saturated sodium bicarbonate solution. The organic phase was washed with brine and concentrated. The resulting product was recrystallized from a methanol-ethyl acetate solvent mixture to yield the analytical material: m.p. 225°–226° C.

HPLC = >99% pure at 214 nm; TLC $R_f$ = 0.40 (EtOAc).

NMR(DMSO-D$_6$): Consistent with structure assignment and confirms presence of solvent.

FAB MS: 400 (M+ +1).

Analysis for $C_{23}H_{21}N_5O_3 \cdot 0.65 H_2O$: Calculated: C, 67.18; H, 5.47; N, 17.03. Found: C, 67.24; H, 5.36; N, 16.64.

EXAMPLE 10

N-{1,3-Dihydro-1-methyl-2-oxo-5-phenyl-1H-1,4-benzodiazepin-3-yl}-N'-{[3-(aminocarbonyl)phenyl]urea}

A suspension of 200 mg of N-{1,3-dihydro-1-methyl-2-oxo-5-phenyl-1H-1,4-benzodiazepin-3-yl}-N'-{[3-(cyano)phenyl]urea} in ice cold methylene chloride was treated with 0.3 ml hydrogen peroxide (30%), 33 mg of tetrabutylammonium hydrogensulfate, and 0.2 ml of sodium hydroxide solution (20%). After 2 hours an additional 0.2 ml of 30% hydrogen peroxide was added and stirring was continued at room temperature for 2 hours more. The reaction mixture was diluted with methylene chloride and and acidified with 1M HCl solution. The organic phase was dried (sodiumسulfate) and concentrated under reduced pressure. The residue was purified via flash column chromatography employing ethyl acetate as eluant to give 60 mg of the title compound: m.p. 182°–184° C.

HPLC = >99% pure at 214 nm; TLC $R_f$ = 0.25 ($CHCl_3$—$CH_3OH$, 9:1).

NMR(DMSO-D$_6$): Consistent with structure assignment and confirms presence of solvent.

FAB MS: 428 (M+ +1).

Analysis for $C_{24}H_{21}N_5O_3 \cdot 0.3$ EtOAc $\cdot 0.75 H_2O$: Calculated: C, 64.75; H, 5.37; N, 14.98. Found: C, 64.71; H, 5.12; N, 14.97.

EXAMPLE 11

N-{1,3-Dihydro-1-methyl-2-oxo-5-phenyl-1H-1,4-benzodiazepin-3-yl}-N'-{[3-(dimethylphosphoramido)phenyl]urea}

N-{1,3-Dihydro-1-methyl-2-oxo-5-phenyl-1H-1,4-benzodiazepin-3-yl}-N'-{[3-(amino)phenyl]urea} (100 mg, 0.25 mmole) was dissolved in 3 ml of tetrahydrofuran. To this solution was added 41.8 µL of triethylamine and dimethyl chlorophosphate. The resulting reaction mixture was protected from moisture and stirred at room temperature overnight. An additional 2 equivalents each of dimethyl chlorophosphate and triethylamine were added and stirring was continued. The reaction mixture was concentrated and the residue was applied to precoated silica gel preparative plates. The product was eluted initially with ethyl acetate and then with chloroform-methanol (9:1): m.p. 182°–184° C.

HPLC = >99% pure at 214 nm; TLC $R_f$ = 0.46 ($CHCl_3$—$CH_3OH$, 9:1).

NMR(DMSO-D$_6$): Consistent with structure assignment and confirms presence of solvent.

FAB MS: 508 (M+ +1).

Analysis for $C_{25}H_{26}N_5O_5P \cdot 1.2$ $CHCl_3 \cdot 2.35 H_2O$: Calculated: C, 45.40; H, 4.64; N, 10.11. Found: C, 45.37; H, 5.00; N, 10.95.

EXAMPLE 12

N-{1,3-Dihydro-1-methyl-2-oxo-5-phenyl-1H-1,4-benzodiazepin-3-yl}-N'-{[3-(aminosulfonamido)phenyl]urea}

A solution of 169 mg of 3-aminosulfonamidoaniline in 5 ml of tetrahydrofuran was stirred magnetically in an ice bath and treated in sequence with triethylamine (126 µL) and triphosgene (89.5 mg) under anhydrous conditions. The pH of the reaction mixture was adjusted to 8 by the addition of an additional 126 µL of triethylamine. After 20 minutes, 200 mg of 3-(R)-amino-1,3-dihydro-1-methyl-5-phenyl-2H-1,4-benzodiazepin-2-one was added and the reaction mixture was stirred at room temperature for 1 hour. The reaction mixture was diluted with ethyl acetate and acidified with 20% acetic acid solution. The mixture was extracted with ethyl acetate and the combined organic extracts were washed with brine, then dried (sodium sulfate) and concentrated under reduced pressure. The residue was chromatographed on silica gel (chloroform-methanol-acetic acid, 90:10:1) to give 105 mg of the title compound: m.p. 167° C. (shrinks);

HPLC = >97% pure at 214 nm; TLC $R_f$ = 0.34 ($CHCl_3$—$CH_3OH$—HOAc, 90:10:1);

NMR(DMSO-D$_6$): Consistent with structure assignment and confirms presence of solvent.

FAB MS: 479 (M+ +1).

Analysis for $C_{23}H_{22}N_6O_4S \cdot 0.20 H_2O \cdot 0.6$ HOAc: Calculated: C, 56.00; H, 4.84; N, 16.13. Found: C, 55.96; H, 4.64; N, 16.14.

EXAMPLE 13

N-{1,3-Dihydro-1-methyl-2-oxo-5-phenyl-1H-1,4-benzodiazepin-3-yl}-N'-{[benzotriazol-3-yl]urea}

A solution of 131 mg of 5-aminobenzotriazole in 3 ml of tetrahydrofuran was stirred magnetically in an ice bath and treated in sequence with triethylamine (136 µL) and triphosgene (96.2 mg) under anhydrous conditions. The pH of the reaction mixture was adjusted to 8 by the addition of an additional 136 µL of triethylamine. After 20 minutes, 200 mg of 3-(R)-amino-1,3-dihydro-1-methyl-5-phenyl-2H-1,4-benzodiazepin-2-one was added and the reaction mixture was stirred at room temperature for 1 hour. The reaction mixture was diluted with ethyl acetate and acidified with 10% citric acid solution. The mixture was extracted with ethyl acetate and the combined organic extracts were washed with brine, then dried (sodium sulfate) and concentrated under reduced pressure. The residue was chromatographed on silica gel (chloroform-methanol-acetic acid, 90:10:1) to give 173 mg of the title compound: m.p. >200° C. (d);

HPLC=>95% pure at 214 nm; TLC $R_f$=0.30 (CHCl$_3$—CH$_3$OH—HOAc, 90:10:1);

NMR(DMSO-D$_6$): Consistent with structure assignment and confirms presence of solvent.

FAB MS: 426 (M$^+$+1).

Analysis for C$_{23}$H$_{19}$N$_7$O$_2$.0.45H$_2$O.1.1HOAc: Calculated: C, 60.58; H, 4.90; N, 19.63. Found: C, 60.57; H, 4.55; N, 19.60.

EXAMPLE 14

N-{1,3-Dihydro-1-methyl-2-oxo-5-phenyl-1H-1,4-benzodiazepin-3-yl}-N'-{[3-(aminosulfonyl)phenyl]urea}

By employing reaction conditions similar to those described in Example 7, except that 3-aminobenzenesulfonamide was substituted for 3-aminobenzonitrile, the title compound was obtained as a white solid in 42% yield after preparative thick layer chromatography: m.p. 185° C. (shrinks);

HPLC=>97% pure at 214 nm; TLC $R_f$=0.32 (CHCl$_3$—CH$_3$OH—HOAc, 90:10:1).

NMR(DMSO-D$_6$): Consistent with structure assignment and confirms presence of solvent.

FAB MS: 464 (M$^+$+1).

Analysis for C$_{23}$H$_{21}$N$_5$O$_3$.0.3HOAc: Calculated: C, 58.86; H, 4.65; N, 14.55. Found: C, 59.22; H, 4.55; N, 14.08.

EXAMPLE 15

N-{1,3-Dihydro-1-methyl-2-oxo-5-phenyl-1H-1,4-benzodiazepin-3-yl}-N'-{[3-phenylboronyl]urea}

By employing reaction conditions similar to those described in Example 7, except that 3-aminobenzeneboronic was substituted for 3-aminobenzonitrile, the title compound was obtained as a white solid after preparative thick layer chromatography using CH$_2$Cl$_2$—CH$_3$OH—HOAc—H$_2$O, 90:10:1:1: m.p. 235° C. (d);

HPLC=>97% pure at 214 nm; TLC $R_f$=0.43 (CH$_2$Cl$_2$—CH$_3$OH—HOAc—H$_2$O, 90:10:1:1).

NMR(DMSO-D$_6$): Consistent with structure assignment and confirms presence of solvent.

FAB MS: 464 (M$^+$+1).

Analysis for C$_{23}$H$_{21}$BN$_4$O$_4$.1.65H$_2$O.0.7CHCl$_3$: Calculated: C, 53.63; H, 4.75; N, 10.56. Found: C, 54.01; H, 5.08; N, 10.16.

EXAMPLE 16

N-{1,3-Dihydro-1-methyl-2-oxo-5-phenyl-1H-1,4-benzodiazepin-3-yl}-N'-{[3-(acetylaminosulfonyl)phenyl]urea}

To a solution of tetrahydrofuran (1.5 ml) containing N-{1,3-dihydro-1-methyl-2-oxo-5-phenyl-1H-1,4-benzodiazepin-3-yl}-N'-}[3-(aminosulfonyl)phenyl]urea} (63 mg) was added 2 equivalents of triethylamine and 1.5 equivalents of acetic anhydride. The reaction mixture was stirred for 6 hours and then was treated with two equivalents each of triethylamine and acetic anhydride. Stirring was continued for 48 hours. The reaction mixture was concentrated and applied to four precoated silica gel preparative plates (0.5 mm thickness). The plates were developed with chloroform-methanol-acetic acid, 90:10:1 to give 55 mg of the title compound as a solid: m.p. 215° C. (d);

HPLC=>97% pure at 214 nm; TLC $R_f$=0.36(CHCl$_3$—CH$_3$OH—HOAc—H$_2$O, 90:10:1:1).

NMR(DMSO-D$_6$): Consistent with structure assignment and confirms presence of solvent.

FAB MS: 506 (M$^+$+1).

Analysis for C$_{25}$H$_{23}$N$_5$O$_5$.0.5H$_2$O.0.6HOAc: Calculated: C, 57.34; H, 4.81; N, 12.76. Found: C, 57.36; H, 4.48; N, 12.78.

EXAMPLE 17

N-{1,3-Dihydro-1-methyl-2-oxo-5-phenyl-1H-1,4-benzodiazepin-3-yl}-N'-{[3-((1H-tetrazol-5-yl)methyl)phenyl]urea}

A solution of 231 mg of 3-amino-[(1H-tetrazole-5-yl)methyl]benzene in 10 ml of tetrahydrofuran was stirred magnetically in an ice bath and treated in sequence with triethylamine (137 μL) and triphosgene (96.9 mg) under anhydrous conditions. The pH of the reaction mixture was adjusted to 8 by the addition of 1.5 equivalents more of triethylamine. After 10 minutes the ice bath was removed, 200 mg of 3-(R)-amino-1,3-dihydro-1-methyl-5-phenyl-2H-1,4-benzodiazepin-2-one was added, and the reaction mixture was stirred at room temperature for 30 minutes. The reaction mixture was concentrated under reduced pressure and the residue was applied to six, 1 mm thick precoated silica gel preparative plates. Elution with chloroform-methanol-acetic acid, 90:10:1) afforded 185 mg of the title compound: m.p. 180° C. (shrinks).

HPLC=99% pure at 214 nm; TLC $R_f$=0.45 (CH$_2$Cl$_2$—CH$_3$OH—HOAc, 90:10:1).

NMR(DMSO-D$_6$): Consistent with structure assignment and confirms presence of solvent.

FAB MS: 467 (M$^+$+1).

Analysis for C$_{25}$H$_{22}$N$_8$O$_2$.0.5 HOAc.0.3H$_2$O: Calculated: C, 62.21; H, 4.94; N, 22.33. Found: C, 62.20; H, 4.74; N, 22.30.

EXAMPLE 18

Synthesis of N-{1,3-Dihydro-1-n-propyl-2-oxo-5-phenyl-1H-1,4-benzodiazepin-3-yl}-N'-{[3-(1H-tetrazol-5-yl)phenyl]urea}

By employing reaction conditions identical to those described in Example 2, except that n-propylbromide was substituted for i-butylbromide, the title compound was obtained as a white solid: m.p. >191° C. (d); [α]$_D$= +5.7° (c=0.07, CH$_3$OH);

HPLC=>98% pure at 214 nm; Chiral purity>99.5%

NMR(DMSO-D$_6$): Consistent with structure assignment and confirms presence of solvent.

FAB MS: 481 (M$^+$+1).

Analysis for C$_{26}$H$_{24}$N$_8$O$_2$.0.35 HOAc.0.7 H$_2$O: Calculated: C, 62.37; H, 5.25; N, 21.80. Found: C, 62.42; H, 5.15; N, 21.79.

EXAMPLE 19

Synthesis of N-{1,3-Dihydro-1-[2-(S)-methylbutyl]-2-oxo-5-phenyl-1H-1,4-benzodiazepin-3-yl}-N'-{[3-(1H-tetrazol-5-yl)phenyl]urea}

By employing reaction conditions identical to those described in Example 2, except that (S)-(+)-1-iodo-2-methylbutane was substituted for i-butylbromide, the title compound was obtained as a white solid:

m.p. 185° C. (shrinks);

HPLC=>96% pure at 214 nm; TLC $R_f=0.40$ (CHCl$_3$—CH$_3$OH—HOAc 90:10:1, v/v).

NMR(DMSO-D$_6$): Consistent with structure assignment and confirms presence of solvent.

FAB MS: 509 (M+ +1).

Analysis for C$_{28}$H$_{28}$N$_8$O$_2$.0.90 HOAc: Calculated: C, 63.61; H, 5.66; N, 19.92. Found: C, 63.70; H, 5.71; N, 19.81.

EXAMPLE 20

Synthesis of N-{1,3-Dihydro-1-cyclopropylmethyl-2-oxo-5-phenyl-1H-1,4-benzodiazepin-3-yl}-N'-{[3-(1H-tetrazol-5-yl)phenyl]urea}

By employing reaction conditions identical to those described in Example 2, except that cyclopropylmethylbromide was substituted for i-butylbromide, the title compound was obtained as a white solid:

m.p. 195° C. (d);

HPLC=>98% pure at 214 nm; TLC $R_f=0.57$ (CHCl$_3$—CH$_3$OH—HOAc 90:10:1, v/v).

NMR(DMSO-D$_6$): Consistent with structure assignment and confirms presence of solvent.

FAB MS: 493 (M+ +1).

Analysis for C$_{27}$H$_{24}$N$_8$O$_2$.0.15 CHCl$_3$.1.55CH$_3$OH: Calculated: C, 61.54; H, 5.46; N, 20.01. Found: C, 61.64; H, 5.15; N, 19.64.

EXAMPLE 21

N-[3(R,S)-2,3-Dihydro-5-(2-fluorophenyl)-1-(2-methylpropyl)-2-oxo-1H-1,4-benzodiazepin-3-yl]-N'-{[3-(tetrazol-5-yl)phenyl]urea}

2-Amino-2-fluorobenzophenone

To a stirred, cooled (4° C.) solution of aniline (10.9 mL, 0.12 mol) in 1,1,2,2-tetrachloroethane (200 mL) was added dropwise a 1M solution of boron trichloride in dichloromethane (130 mL, 0.13 mol) followed by a solution of 2-fluorobenzonitrile (17.3 mL, 0.16 mol) in 1,1,2,2-tetrachloroethane (50 mL) then aluminium trichloride (17.33 g, 0.13 mol). The reaction mixture was heated to 100° C. in order to distill the majority of the dichloromethane then the mixture was heated at 150° C. (oil bath temperature) for 5 hours. After cooling to 4° C. 2M HCl (100 mL) was added cautiously and the mixture was heated to 100° C. (oil bath temperature) for 30 minutes. The mixture was cooled to room temperature then diluted with dichloromethane (200 mL) and filtered. The organic layer was separated, washed with water (2×200 mL), dried (sodium sulphate) then evaporated in vacuo to afford an orange solid (12.95 g) which was recrystallized from ethanol to give the title compound as a yellow crystalline solid (10.80 g, 42%): mp 127°–128° C. $R_f$0.61 in ethyl acetate/n-hexane (1:1) on silica.

2-[(2-Bromoacetyl)amino]-2-fluorobenzophenone

To a cooled (−10° C.), stirred suspension of 2-amino-2-fluorobenzophenone (19.40 g, 0.090 mol) in dichloromethane (130 mL) and water (10 mL) was added a solution of bromoacetylbromide (9.0 mL, 0.104 mol) in dichloromethane (30 mL), keeping the temperature of the reaction mixture at −10° C. After addition the reaction mixture was stirred whilst warming to room temperature (2½ hours). The organic layer was collected, washed with water (2×100 mL) then concentrated to approximately 70 mL. Hexane (70 mL) was added and the required product collected by filtration (25.6 g, 83%): mp 120°–121° C. $R_f$0.30 in diethyl ether/n-hexane (1:1) on silica; $^1$H NMR (CDCl$_3$) δ4.05 (2H,s), 7.10–7.64 (7H, m), 8.70 (1H, d, J=8 Hz), 11.95 (1H, broad s); MS, m/z 335 (M+). Anal. Calcd. for C$_{15}$H$_{11}$BrFNO$_2$:C, 53.59; H, 3.30; N, 4.17. Found: C, 53.32; H, 3.33; N, 4.00.

1,3-Dihydro-5-(2-fluorophenyl)-2H-1,4-benzodiazepin-2-one

Anhydrous ammonia gas was bubbled through a stirred, cooled (−10° C.) suspension of 2-[(2-bromoacetyl)amino]-2-fluorobenzophenone (25.0 g, 0.074 mol) in methanol (460 mL), keeping the reaction mixture temperature below 10° C. After the mixture was saturated (2 hours) it was stirred whilst warming to room temperature over 1 hour, then heated to reflux for 2 hours. The methanol was evaporated to afford an orange solid which was re-dissolved in hot methanol (80 mL), filtered then diluted with water (80 mL) in portions to promote crystallization. After ageing at 4° C. for 1 hour the required product was collected by filtration and dried over phosphorus pentoxide in vacuo (17.6 g, 93%):mp 181°–182° C. $R_f$0.30 in ethyl acetate/n-hexane (1:1) on silica; $^1$H NMR (CDCl$_3$) δ4.38 (2H, s), 7.02–7.60 (8H, m), 8.74 (1H, broad s); MS, m/z 254 (M+). Anal. Calcd. for C$_{15}$H$_{11}$FN$_2$O: C, 70.86; H, 4.36; N, 11.02. Found: C, 71.09; H, 4.29; N, 11.13.

1,3-Dihydro-5-(2-fluorophenyl)-2H-1-(2-methylpropyl)-1,4-benzodiazepin-2-one

Sodium hydride (2.57 g of a 55% oil dispersion, 0.059 mol) was added in portions to a stirred, cooled (0° C.) solution of 1,3-dihydro-5-(2-fluorophenyl)-2H-1,4-benzodiazepin-2-one (15.0 g, 0.059 mol) in anhydrous dimethylformamide (230 mL), under a nitrogen atmosphere. The reaction mixture was stirred at 0° C. for 20 minutes then 1-iodo-2-methylpropane (7.0 mL, 0.061 mol) was added dropwise. After a further 1 hour at 0° C. the mixture was stirred at room temperature for 20 hours. Water (5 mL) was added then the mixture evaporated to dryness in vacuo. The residue was partitioned between ethyl acetate (250 mL) and water (150 mL). The organic layer was separated, washed with water (100 mL), brine (100 mL) then dried (sodium sulphate) and evaporated to give an orange oil which was purified by column chromatography on silica using ethyl acetate/n-hexane (1:2) to (1:1) (gradient). The title compound was obtained as a viscous yellow gum (13.60 g, 74%). $R_f$0.45 in ethyl acetate/n-hexane (1:1) on silica; $^1$H NMR (CDCl$_3$) δ0.72 (3H, d, J=6.5 HZ), 0.82 (3H, d, J=6.5 Hz), 1.70–1.82 (1H, m), 3.45 (1H, dd, J$_1$=5, J$_2$=14 Hz), 3.79 (1H, d, J=10.5 Hz), 4.37 (1H, dd, J$_1$=10, J$_2$=14 Hz), 4.85 (1H, d, J=10.5 Hz), 7.02–7.72 (8H, m); MS, m/z 310 (M+). Anal. Calcd. for C$_{19}$H$_{19}$FN$_2$O.0.33H$_2$O: C, 72.15; H, 6.27; N, 8.86. Found: C, 71.91; H, 6.02; N, 8.72.

1,3-Dihydro-5-(2-fluorophenyl)-1-(2-methylpropyl)-3-oximido-2H-1,4-benzodiazepin-2-one Potassium t-butoxide (12.83 g, 0.105 mol) was added in portions to a stirred, cooled (−20° C.) solution of 1,3-dihydro-5-(2-fluorophenyl)-2H-1-(2-methylpropyl)-1,4-benzodiazepin-2-one (13.18 g, 0.042 mol) in anhydrous toluene (200 mL), under a nitrogen atmosphere. After stirring at −20° C. for a further 5 minutes isopentylnitrite (6.7 mL, 0.050 mol) was added dropwise keeping the temperature of the reaction mixture below −15° C. After a further 30 minutes the mixture was poured onto a cooled (4° C.), vigorously stirred mixture of ethyl acetate (200 mL) and 1M citric acid (200 mL). The organic layer was separated and the aqueous extracted with ethyl acetate (200 mL). The combined organics were washed with water (2×200 mL), dried (sodium sulphate) then evaporated to dryness. The residue was treated with toluene (50 mL) and n-hexane (150 mL) and the required product was collected by filtration (11.50 g, 81%): mp 220°–223° C. $R_f$0.45 in ethyl acetate/n-hexane (1:1) on silica; $^1$H NMR (CDCl$_3$) δ0.72–0.95 (6H, m), 1.80–1.92 (1H, m), 3.50–3.58 (1H, m), 4.42–4.50 (1H, m), 6.94–7.50 (8H, m); MS, m/z 339 (M$^+$); IR (nujol) 3350, 1650 and 1595 cm$^{-1}$. Anal. Calcd. for C$_{19}$H$_{18}$FN$_3$O$_2$: C, 67.24; H, 5.35; N, 12.38. Found: C, 67.39; H, 5.59; N, 12.05.

3(R,S)-Amino-1,3-dihydro-5-(2-fluorophenyl)-1-(2-methylpropyl)-2H-1,4-benzodiazepin-2-one 1,3-Dihydro-5-(2-fluorophenyl)-1-(2-methylpropyl)-3-oximido-2H-1,4-benzodiazepin-2-one (11.5 g, 0.034 mol) was hydrogenated in methanol (1.5L) with 5% ruthenium on carbon (3 g) at 40 psi, with heating to 70° C., for 24 hours. A further quantity of 5% ruthenium on carbon (1 g) was added and the mixture hydrogenated for another 24 hours. The mixture was filtered and the solvent evaporated to afford the title amine as a viscous gum (11.8 g). $^1$H NMR (D$_6$-DMSO) δ0.58 (3H, d, J=6.5 Hz), 0.77 (3H, d, J=6.5 Hz), 1.50–1.64 (1H, m), 3.65 (1H, dd, J$_1$=5, J$_2$=14 Hz), 4.20 (1H, dd, J$_1$=10, J$_2$=14 Hz), 4.28 (1H, s), 7.16–7.72 (8H, m).

5-(3-Nitrophenyl)tetrazole

To a solution of 3-cyanonitrobenzene (20 g, 0.13 mol) in 1-methyl-2-pyrrolidinone (200 mL) was added triethylamine hydrochloride (27.9 g, 0.20 mol) followed by sodium azide (26.4 g, 0.40 mol). The mixture was heated at 160° C. for 1.5 hours, then cooled to ambient temperature, poured into ice water (1000 mL) and acidified using 5M HCl. The solid which precipitated from the mixture was filtered, washed with water and dried under vacuum at 50° C. to afford the title tetrazole (22.1 g, 86%) as a beige powder; mp 154°–156° C. $^1$H NMR (CDCl$_3$) δ7.59 (1H, dd, J=8 Hz), 8.19 (1H, d, J=8 Hz), 8.36 (1H, d, J=8 Hz), 8.86 (1H, s).

5-(3-Aminophenyl)tetrazole hydrochloride

To a solution of 5-(3-nitrophenyl)tetrazole (22 g, 0.12 mol) in ethanol (500 mL) was added 10% palladium on carbon (1.5 g, 7% (w/w)) in hydrochloric acid (23 mL of a 5M solution). The mixture was hydrogenated at 40 psi for 10 minutes then the catalyst filtered off and washed with water. The solvents were evaporated in vacuo and the brown solid azeotroped with toluene (4×100 mL). The resulting solid was triturated with hot ethanol to give 5-(3-aminophenyl)tetrazole hydrochloride (16.3 g, 71%) as a beige powder. mp 203°–205° C. $^1$H NMR (D$_2$O) δ7.63 (1H, d, J=8 Hz), 7.75 (1H, dd, J=8 Hz), 8.00 (2H, m).

N-(3(R,S)-2,3-Dihydro-5-(2-fluorophenyl)-1-(2-methylpropyl)-2-oxo-1H-1,4-benzodiazepin-3-yl]-N'-[3-(tetrazol-5-yl)phenyl]urea Triethylamine (286 μL, 2.1 mmol) was added to a stirred suspension of 5-(3-aminophenyl)tetrazole hydrochloride (219 mg, 1.03 mmol) in anhydrous tetrahydrofuran (10 mL), under a nitrogen atmosphere. The suspension was cooled (4° C.) and triphosgene (102 mg, 0.34 mmol) was added followed by further triethylamine (143 μL, 1.02 mmol). The cooling bath was removed and the suspension was stirred at room temperature for 30 minutes. A solution of 3(R,S)-amino-1,3-dihydro-5-(2-fluorophenyl)-1-(2-methylpropyl)-2H-1,4-benzodiazepin-2-one (230 mg, 0.71 mmol) in anhydrous tetrahydrofuran (10 mL) was added and the reaction mixture was stirred at room temperature for an hour. Ethyl acetate (20 mL) was added and the mixture acidified with 20% aqueous acetic acid. The organic layer was separated and the aqueous was extracted with ethyl acetate (2×20 mL). The combined organics were washed with brine, then dried (sodium sulphate) and evaporated to afford a colourless solid. This solid was triturated with methanol then purified by column chromatography on silica using tetrahydrofuran—0.5% acetic acid in tetrahydrofuran. The solid obtained was further triturated with methanol to afford the title compound as a colourless solid (90 mg, 25%): mp >185° C. (dec.). $R_f$0.65 in 0.5% acetic acid/tetrahydrofuran on silica; $^1$H NMR (d$_6$-DMSO) δ0.62 (3H, d, J=7 Hz), 0.80 (3H, d, J=7 Hz), 1.52–1.68 (1H, m), 3.72 (1H, dd, J$_1$=5, J$_2$=14 Hz), 4.23 (1H, dd, J$_1$=10, J$_2$=14 Hz), 5.28 (1H, s), 7.24–7.81 (11H, m), 8.22 (1H, dd, J$_1$=2, J$_2$=2 Hz), 9.40 (1H, s); MS, FAB$^+$, m/z 513 (M+H)$^+$. Anal. Calcd. for C$_{27}$H$_{25}$FN$_8$O$_2$.2H$_2$O: C, 59.11; H, 5.33; N, 20.43. Found: C, 58.99; H, 4.98 N, 20.25.

EXAMPLE 22

Synthesis of N-{1,3-Dihydro-1-methyl-2-oxo-5-phenyl-1H-1,4-benzodiazepin-3-yl}-N'-{[3-(N-acetylcarboxamido)phenyl]urea}

3-Nitro-N-(acetyl)phenylcarboxamide

A solution of 3-nitrophenylcarboxamide (2 g) in 125 ml of dry methylene chloride was cooled to 0° C. and mixed with 1.25 ml of acetic anhydride and 2.1 g of 4-N,N-dimethylaminopyridine. The reaction mixture was warmed to room temperature and stirred for 1 hour. Additional amounts of 4-N,N-dimethylaminopyridine (809 mg) and acetic anhydride (1.25 ml) were added to the reaction mixture and stirring was continued overnight. The reaction mixture was diluted with 300 ml of methylene chloride and was washed with 60 ml of 5% citric acid solution. The organic extracts were dried, concentrated in vacuo, and the residue was chromatographed on silica gel (chloroform-methanol, 97:3 v/v) to yield 500 mg of the title compound in pure form.

3-Amino-N-(acetyl)phenylcarboxamide

3-Nitro-N-(acetyl)phenylcarboxamide (200 mg) was dissolved in 60 ml of ethanol, treated with 200 mg of 10% palladium/carbon catalyst, and hydrogenated on a Parr apparatus at 30 psi for 15 minutes. The reaction mixture was filtered through Celite and concentrated to give the title compound in quantitative yield as a white solid.

N-{1,3-Dihydro-1-methyl-2-oxo-5-phenyl-1H-1,4-benzodiazepin-3-yl}-N'-{[3-(N-(acetyl)carboxamido)-phenyl]urea}

A solution of 213 mg of 3-amino-N-(acetyl)phenylcarboxamide in 10 ml of tetrahydrofuran was stirred magnetically in an ice bath and treated with triphosgene (118 mg). Triethylamine was added in three equal portions (100 mL) over a ten minute period. The pH of the reaction mixture was approximately 7 (moist pH paper) and was adjusted to 8 by the addition of 50 μL more of triethylamine. After 5 minutes at 0° C., the reaction mixture was warmed to room temperature for 5 minutes, recooled to 0° C. and treated with a solution of 2 ml tetrahydrofuran containing 213 mg of 3-(R)-amino-1,3-dihydro-1-methyl-5-phenyl-2H-1,4-benzodiazepin-2-one. The reaction mixture was warmed to room temperature, stirred for 40 minutes, and filtered. The filtrate was concentrated under reduced pressure and was then azeotropically dried with toluene. The residue was chromatographed on six 1 mm precoated silica gel plates (chloroform-methanol-acetic acid, 93:7:0.75, v/v elution) to afford 243 mg of the title compound: m.p. 176° C. (d).

HPLC=98.9% pure at 214 nm; TLC $R_f$=0.29 (CHCl$_3$—CH$_3$OH, 9:1).

NMR(DMSO-D$_6$): Consistent with structure assignment and confirms presence of solvent.

FAB MS: 470 (M+ +1).

Analysis for C$_{26}$H$_{23}$N$_5$O$_4$.0.45 EtOAc: Calculated: C, 65.58; H, 5.27; N, 13.76. Found: C, 65.53; H, 5.22; N, 13.81.

EXAMPLE 23

Synthesis of
N-{1,3-Dihydro-1-methyl-2-oxo-5-phenyl-1H-1,4-benzodiazepin-3-yl}-N'-{[3-(N-(methanesulfonyl)carboxamido)phenyl]urea}

3-Nitro-N-(methanesulfonyl)phenylcarboxamide

A solution of 3-nitrophenylcarboxamide (2 g) in 150 ml of dry tetrahydrofuran was cooled to 0° C. and treated with 609 mg of sodium hydride (60% oil dispersion). The reaction mixture was stirred for 20 minutes and then methanesulfonylchloride (1.18 ml) was introduced dropwise via syringe. After 5 minutes the reaction mixture became homogeneous and was warmed to room temperature and stirred overnight. The reaction mixture was diluted with 300 ml of ethyl acetate and was washed with brine. The organic extracts were dried, concentrated in vacuo, and the residue was chromatographed on silica gel (ethyl acetate then chloroform-methanol, 95:5 v/v) to yield 1.6 g of the title compound in pure form.

3-Amino-N-(methansulfonyl)phenylcarboxamide

3-Nitro-N-(methanesulfonyl)phenylcarboxamide (1.6 g) was dissolved in 50 ml of ethanol, treated with 510 mg of 10% palladium/carbon catalyst, and hydrogenated on a Parr apparatus at 30 psi for 15 minutes. The reaction mixture was filtered through Celite and concentrated to give the title compound (1.1 g) as a white solid.

N-{1,3-Dihydro-1-methyl-2-oxo-5-phenyl-1H-1,4-benzodiazepin-3-yl}-N'-{[3-(N-(methanesulfonyl)carboxamido)phenyl]urea}

The title compound was obtained employing reaction conditions identical to those described in Example 22 except that 3-amino-N-(methanesulfonyl)phenylcarboxamide was substituted for 3-amino-N-(acetyl)phenyl carboxamide:

HPLC=98.3% pure at 214 nm; TLC $R_f$=0.27 (CHCl$_3$—CH$_3$OH, 9:1).

NMR(DMSO-D$_6$): Consistent with structure assignment and confirms presence of solvent.

FAB MS: 506 (M+ +1).

Analysis for C$_{25}$H$_{23}$N$_5$O$_5$S.0.25 CH$_3$OH.0.55 CHCl$_3$: Calculated: C, 53.50; H, 4.27; N, 12.09. Found: C, 53.48; H, 4.10; N, 11.75.

EXAMPLE 24

Synthesis of
N-{1,3-Dihydro-1-methyl-2-oxo-5-phenyl-1H-1,4-benzodiazepin-3-yl}-N'-{[3-(N-(2-propylsulfonyl)carboxamido)phenyl]urea}

3-Nitro-N-(2-propylsulfonyl)phenylcarboxamide

A solution of 3-nitrophenylcarboxamide (2 g) in 150 ml of dry tetrahydrofuran was cooled to 0° C. and treated with 530 mg of sodium hydride (60% oil dispersion). The reaction mixture was stirred for 20 minutes and then 2-propylsulfonylchloride (1.5 ml) was introduced dropwise via syringe. After 5 minutes the reaction mixture became homogeneous and was warmed to room temperature and stirred for 2 hours. The reaction mixture was diluted with 300 ml of ethyl acetate and was washed with brine. The organic extracts were dried, concentrated in vacuo, and the residue was chromatographed on silica gel (chloroform-methanol, 95:5 v/v) to yield 0.6 g of the title compound in pure form.

3-Amino-N-(2-propylsulfonyl)phenylcarboxamide

3-Nitro-N-(2-propylsulfonyl)phenylcarboxamide (0.6 g) was dissolved in 30 ml of ethanol, treated with 300 mg of 10% palladium/carbon catalyst, and hydrogenated on a Parr apparatus at 30 psi for 15 minutes. The reaction mixture was filtered through Celite and concentrated to give the title compound (307 mg) as a solid.

N-{1,3-Dihydro-1-methyl-2-oxo-5-phenyl-1H-1,4-benzodiazepin-3-yl}-N'-{[3-(N-(2-propylsulfonyl)carboxamido)phenyl]urea}

The title compound was obtained employing reaction conditions identical to those described in Example 22 except that 3-amino-N-(2-propylsulfonyl)phenylcarboxamide was substituted for 3-amino-N-(acetyl)phenyl carboxamide: m.p. 198°-200° C.

HPLC=95% pure at 214 nm; TLC $R_f$=0.31 (CHCl$_3$—CH$_3$OH, 9:1).

NMR(DMSO-D$_6$): Consistent with structure assignment and confirms presence of solvent.

FAB MS: 534 (M+ +1).

Analysis for C$_{27}$H$_{27}$N$_5$O$_5$S.0.1 CHCl$_3$.0.25 CH$_3$OH: Calculated: C, 59.40; H, 5.10; N, 12.69. Found: C, 59.35; H, 4.85; N, 12.72.

EXAMPLE 25

Synthesis of
N-{1,3-Dihydro-1-methyl-2-oxo-5-phenyl-1H-1,4-benzodiazepin-3-yl}-N'-{[3-(N-(t-butylsulfonyl)carboxamido)phenyl]urea}

The title compound was obtained employing reaction conditions identical to those described in Example 22 except that 3-amino-N-(t-butylsulfonyl)phenylcarboxamide was substituted for 3-amino-N-(acetyl)phenyl carboxamide: m.p. 204°-205° C.

HPLC=>99% pure at 214 nm; TLC $R_f$=0.65 (CH$_2$Cl$_2$—CH$_3$OH—HOAc—H$_2$O, 90:10:1:1).

NMR(DMSO-D$_6$): Consistent with structure assignment and confirms presence of solvent.

Analysis for C$_{25}$H$_{23}$N$_5$O$_5$S.0.1 H$_2$O: Calculated: C, 61.21; H, 5.36; N, 12.75. Found: C, 61.18; H, 5.34; N, 12.9.

EXAMPLE 26

Synthesis of
N-{1,3-Dihydro-1-methyl-2-oxo-5-phenyl-1H-1,4-benzodiazepin-3-yl}-N'-{[3-(N-(2-propylaminocarbonyl)-carboxamido)phenyl]urea}

3-Nitro-N-(2-propylaminocarbonyl)phenylcarboxamide

A solution of 3-nitrophenylcarboxamide (2 g) in 25 ml of dry tetrahydrofuran was cooled to 0° C. and treated with 648 mg of sodium hydride (60% oil dispersion). The reaction mixture was stirred for 15 minutes and then 2-propylisocyanate (1.48 ml) was introduced dropwise via syringe. The reaction mixture was then stirred at 0° C. overnight. The reaction mixture was diluted with 300 ml of ethyl acetate. The reaction mixture was washed with 10% citric acid solution and brine. The organic extracts were dried and then concentrated in vacuo to yield 3.9 g of the title compound in sufficient purity to be used in the next step.

3-Amino-N-(2-propylaminocarbonyl)phenylcarboxamide 3-Nitro-N-(2-propylaminocarbonyl)phenylcarboxamide (1.5 g) was dissolved in 150 ml of ethanol, treated with 850 mg of 10% palladium/carbon catalyst, and hydrogenated on a Parr apparatus at 30 psi for 10 minutes. The reaction mixture was filtered through Celite and concentrated to give the title compound (1.1 g) as a solid.

N-{1,3-Dihydro-1-methyl-2-oxo-5-phenyl-1H-1,4-benzodiazepin-3-yl}-N'-{[3-(N-(2-propylaminocarbonyl)-carboxamido)phenyl]urea}

The title compound was obtained employing reaction conditions identical to those described in Example 22 except that 3-amino-N-(2-propylaminocarbonyl)-phenylcarboxamide was substituted for 3-amino-N-(acetyl)phenylcarboxamide: m.p. 159°–162° C. (ethyl acetate-hexane).

HPLC=99.1% pure at 214 nm; TLC $R_f$=0.30 (EtOAc-hexane, 2:1).

NMR(DMSO-$D_6$): Consistent with structure assignment and confirms presence of solvent.

FAB MS: 513 (M+ +1).

Analysis for $C_{28}H_{28}N_6O_4 \cdot 1.5\ H_2O$: Calculated: C, 62.32; H, 5.79; N, 15.58.

EXAMPLE 27

Synthesis of
N-{1,3-Dihydro-1-cyclopropylmethyl-2-oxo-5-phenyl-1H-1,4-benzodiazepin-3-yl}-N'-{[3-(N-(acetyl)sulfonamido)phenyl]urea}

3-Nitro-N-(acetyl)benzenesulfonamide

A solution of 3-nitrobenzenesulfonamide (615 mg) in 10 ml of dry tetrahydrofuran was cooled to 0° C. and mixed with 0.34 ml of acetic anhydride and 166 mg of 4-N,N-dimethylaminopyridine. The reaction mixture was stirred for 30 minutes, quenched with 10% citric acid solution, and diluted with ethyl acetate. The reaction mixture was extracted with ethyl acetate. The organic extracts were washed with brine, dried, concentrated in vacuo to yield 946 mg of the title compound in pure form.

3-Amino-N-(acetyl)benzenesulfonamide

3-Nitro-N-(acetyl)benzenesulfonamide (452 mg) was dissolved in 40 ml of ethanol, treated with 10% palladium/carbon catalyst, and hydrogenated on a Parr apparatus at 30 psi for 15 minutes. The reaction mixture was filtered through Celite and concentrated to give 564 mg of a waxy solid. The title compound was obtained analytically pure after column chromatography on silica gel (chloroform-methanol, 9:1 v/v).

N-{1,3-Dihydro-1-cyclopropylmethyl-2-oxo-5-phenyl-1H-1,4-benzodiazepin-3-yl}-N'-{[3-(N-(acetyl)sulfonamido)phenyl]urea}

The title compound was obtained from 359 mg of 3-amino-N-(acetyl)benzenesulfonamide and 331 mg of 3-(R)-amino-1,3-dihydro-1-cyclopropylmethyl-5-phenyl-2H-1,4-benzodiazepin-2-one according to the reaction conditions described in Examples 2 and 22: m.p. 203° C. (d).

HPLC=98.3% pure at 214 nm; TLC $R_f$=0.40 ($CH_2Cl_2$—$CH_3OH$—HOAc—$H_2O$, 90:10:1:1).

NMR(DMSO-$D_6$): Consistent with structure assignment and confirms presence of solvent.

FAB MS: 546 (M+ +1).

Analysis for $C_{28}H_{27}N_5O_5S \cdot 0.4$ HOAc: Calculated: C, 60.72; H, 5.06; N, 12.30.

EXAMPLE 28

Synthesis of
N-{1,3-Dihydro-1-methyl-2-oxo-5-phenyl-1H-1,4-benzodiazepin-3-yl}-N'-{[3-(N-(1,1-dimethylethylcarbonyl)sulfonamido)phenyl]urea}

The title compound was obtained employing reaction conditions identical to those described in Example 22 except that 3-amino-N-(1,1-dimethylethylcarbonyl)benzenesulfonamide was substituted for 3-amino-N-(acetyl)phenylcarboxamide: m.p. 195°–197° C.

HPLC=>99% pure at 214 nm; TLC $R_f$=0.25 ($CHCl_3$—$CH_3OH$, 96:4).

NMR(DMSO-$D_6$): Consistent with structure assignment and confirms presence of solvent.

FAB MS: 548 (M+ +1).

Analysis for $C_{28}H_{29}N_5O_5S \cdot 0.3\ CH_3OH \cdot 0.35\ CHCl_3$: Calculated: C, 57.44; H, 5.14; N, 11.69. Found: C, 57.46; H, 4.89; N, 11.63.

EXAMPLE 29

Synthesis of
N-{1,3-Dihydro-1-methyl-2-oxo-5-phenyl-1H-1,4-benzodiazepin-3-yl}-N'-{[3-(N-(2,2-dimethylcyclopropylcarbonyl)sulfonamido)phenyl]urea}

The title compound was obtained employing reaction conditions identical to those described in Example 22 except that 3-amino-N-(2,2-dimethylcyclopropylcarbonyl)benzenesulfonamide was substituted for 3-amino-N-(acetyl)phenylcarboxamide:

HPLC=>95% pure at 214 nm; TLC $R_f$=0.16 ($CHCl_3$—$CH_3OH$, 95:5).

NMR(DMSO-$D_6$): Consistent with structure assignment and confirms presence of solvent.

FAB MS: 560 (M+ +1).

Analysis for $C_{29}H_{29}N_5O_5S \cdot 0.4\ CH_3OH \cdot 0.25\ CHCl_3$: Calculated: C, 59.12; H, 5.16; N, 11.63.

EXAMPLE 30

Synthesis of
N-{1,3-Dihydro-1-methyl-2-oxo-5-phenyl-1H-1,4-benzodiazepin-3-yl}-N'-{[3-(N-(t-butylaminocarbonyl)sulfonamido)phenyl]urea}

The title compound was obtained employing reaction conditions identical to those described in Example 22 except that 3-amino-N-(t-butylaminocarbonyl)benzenesulfonamide was substituted for 3-amino-N-(acetyl)phenylcarboxamide: m.p. 168°–170° C. HPLC=>96% pure at 214 nm; TLC $R_f$=0.27 ($CHCl_3$—$CH_3OH$, 95:5).

NMR(DMSO-$D_6$): Consistent with structure assignment and confirms presence of solvent.

FAB MS: 563 (M+ +1).

Analysis for $C_{28}H_{30}N_6O_5S \cdot 0.5$ dioxane $\cdot 0.7\ CF_3CO_2H$: Calculated: C, 57.02; H, 5.35; N, 13.00. Found: C, 57.01; H, 5.49; N, 12.97.

EXAMPLE 31

Synthesis of N-{1,3-Dihydro-1-methyl-2-oxo-5-phenyl-1H-1,4-benzodiazepin-3-yl}-N'-{[3-(N-(diphenylphosphono)sulfonamido)phenyl]urea}

The title compound was obtained employing reaction conditions identical to those described in Example 22 except that 3-amino-N-(diphenylphosphono)benzenesulfonamide was substituted for 3-amino-N-(acetyl)phenylcarboxamide: m.p. 195°–200° C.

HPLC=>97% pure at 214 nm; TLC $R_f$=0.19 (CHCl$_3$—CH$_3$OH, 9:1).

NMR(DMSO-D$_6$): Consistent with structure assignment and confirms presence of solvent.

FAB MS: 696 (M+ +1).

Analysis for C$_{35}$H$_{30}$N$_5$O$_7$PS.0.6 CHCl$_3$.0.5CH$_3$OH: Calculated: C, 55.35; H, 4.19; N, 8.94. Found: C, 55.34; H, 4.15; N, 8.96.

EXAMPLE 32

Synthesis of N-{1,3-Dihydro-1-methyl-2-oxo-5-phenyl-1H-1,4-benzodiazepin-3-yl}-N'-{[3-(trans-carboxyethylene)phenyl]urea}

The title compound was obtained employing reaction conditions identical to those described in Example 22 except that 3-amino-trans-cinnamic acid was substituted for 3-amino-N-(acetyl)phenylcarboxamide: m.p. 196° C. (d).

HPLC=>98% pure at 214 nm; TLC $R_f$=0.26 (CH$_2$Cl$_2$—CH$_3$OH—HOAc—H$_2$O, 95:5:0.5:0.5).

NMR(DMSO-D$_6$): Consistent with structure assignment and confirms presence of solvent.

FAB MS: 455 (M+ +1).

Analysis for C$_{26}$H$_{22}$N$_4$O$_4$.0.6H$_2$O: Calculated: C, 67.12; H, 5.03; N, 12.04. Found: C, 67.1; H, 4.93; N, 12.02.

EXAMPLE 33

Synthesis of N-{1,3-Dihydro-1-methyl-2-oxo-5-phenyl-1H-1,4-benzodiazepin-3-yl}-N'-{[3-(2-methyltetrazol-5-yl)phenyl]urea}

3-Nitro-(2-methyltetrazol-5-yl)benzene

3-Nitro-(1H-tetrazol-5-yl)benzene (0.99 g) was added at 0° C. to a magnetically stirred suspension of sodium hydride (243 mg, 60% oil dispersion) in 50 ml of dry tetrahydrofuran. The reaction mixture was stirred for 15 minutes and then iodomethane was added in 6 increments of 0.5 ml over a 3 hour period. The reaction mixture was concentrated in vacuo and the residue was partitioned between water (50 ml) and ethyl acetate. The aqueous layer was extracted (2×15 ml) with ethyl acetate and the combined organic extracts were washed with brine, dried, and concentrated. The title compound was obtained as a solid after flash chromatography on silica gel (chloroform-methanol, 95:5).

3-Amino-(1H-tetrazole-5-yl)benzene

3-Nitro-(2-methyltetrazol-5-yl)benzene (648 mg) was dissolved in 100 ml of ethanol, treated with 0.283 g of 10% palladium/carbon catalyst, and hydrogenated on a Parr apparatus at 30 psi for 15 minutes. The reaction mixture was filtered through Celite and concentrated to give 0.469 g of the title compound.

N-{1,3-Dihydro-1-methyl-2-oxo-5-phenyl-1H-1,4-benzodiazepin-3-yl}-N'-{[3-(2-methyltetrazol-5-yl)phenyl]urea}

The title compound was obtained employing reaction conditions identical to those described in Example 22 except that 3-amino-(2-methyltetrazol-5-yl)benzene was substituted for 3-amino-N-(acetyl)phenylcarboxamide. Flash column chromatography of the crude reaction product on silica gel (methylene chloride-methanol-acetic acid-water, 96:4:0.4:0.4, v/v elution) afforded the title compound: m.p. 155° C. (d).

HPLC=<99% pure at 214 nm; TLC $R_f$=0.66 (CH$_2$Cl$_2$—CH$_3$OH—HOAc, 90:10:1).

NMR(DMSO-D$_6$): Consistent with structure assignment and confirms presence of solvent.

FAB MS: 467 (M+ +1).

Analysis for C$_{25}$H$_{22}$N$_8$O$_2$.0.45CHCl$_3$.0.4CH$_3$OH: Calculated: C, 58.24; H, 4.55; N, 21.02. Found: C, 58.28; H, 4.20; N, 21.74.

EXAMPLE 34

Synthesis of N-{1,3-Dihydro-1-methyl-2-oxo-5-phenyl-1H-1,4-benzodiazepin-3-yl}-N'-{[3-(1,2,4-oxadiazol-5-one)phenyl]urea}

3-(tert-Butyloxycarbonylamino)benzenylamidoxime

Hydroxylamine hydrochloride (477 mg) was added to a solution of 50 ml of sodium ethoxide (containing 158 mg of sodium). After 20 minutes, 3-(tert-butyloxycarbonylamino)benzonitrile (1.0 g) was added and the reaction mixture was refluxed overnight. The reaction mixture was concentrated in vacuo and the residue was partitioned between water (50 ml) and ethyl acetate. The aqueous layer was extracted (2×15 ml) with ethyl acetate and the combined organic extracts were washed with brine, dried, and concentrated to give 1.01 g of crude product. The title compound was obtained as a white solid after flash chromatography on silica gel (chloroform-methanol, 9:1).

3-(tert-Butyloxycarbonylamino)benzene-1,2,4-oxadiazol-5-one 3-(tert-Butyloxycarbonylamino)benzenylamidoxime (300 mg) was dissolved in tetrahydrofuran and the solution was cooled to 0° C. Triphosgene (142 mg) was added, followed by sufficient amounts of triethylamine to raise the pH of the reaction mixture to approximately 8. The ice bath was removed and the reaction mixture was stirred for 20 minutes at room temperature. The reaction mixture was partitioned between ethyl acetate and 10% citric acid solution. The organic phase was washed with brine, then dried, and concentrated. The title compound was obtained in homogeneous form after preparative chromatography on silica gel (ethyl acetate-hexane, 2:1).

3-Aminobenzene-1,2,4-oxadiazol-5-one hydrochloride

A solution of ethyl acetate (10 ml) containing 150 mg of 3-(tert-butyloxycarbonylamino)benzene-1,2,4-oxadiazol-5-one was cooled to 0° C. and treated with a continuous stream of hydrogen chloride gas for 10 minutes. The reaction mixture was stirred for 30 minutes more and the solvent and excess hydrogen chloride were removed under reduced pressure. The residue was azeotropically dried with toluene to give 120 mg of the title compound in sufficient purity to continue directly to the next step.

N-{1,3-Dihydro-1-methyl-2-oxo-5-phenyl-1H-1,4-benzodiazepin-3-yl}-N'-{[3-(1,2,4-oxadiazol-5-one)phenyl]urea}

The title compound was obtained employing reaction conditions identical to those described in Example 22 except that 3-aminobenzene-1,2,4-oxadiazol-5-one hydrochloride was substituted for 3-amino-N-(acetyl)-phenylcarboxamide. Preparative thick layer chromatography of the crude reaction product on silica gel (chloroform-methanol, 9:1, v/v elution) afforded the title compound: m.p. 190° C. (d).

HPLC= >96% pure at 214 nm; TLC $R_f$=0.43 ($CH_2Cl_2$—$CH_3OH$—HOAc—$H_2O$, 90:10:1:1).

NMR(DMSO-$D_6$): Consistent with structure assignment and confirms presence of solvent.

FAB MS: 469 ($M^+$ +1).

Analysis for $C_{25}H_{20}N_6O_4 \cdot 1.85H_2O$: Calculated: C, 58.12; H, 4.63; N, 16.17. Found: C, 58.05 H, 4.40; N, 16.25.

EXAMPLE 35

Synthesis of
N-{1,3-Dihydro-1-cyclopropylmethyl-2-oxo-5-phenyl-1H-1,4-benzodiazepin-3-yl}-N'-{[3-(1,2,4-oxadiazol-5-one)phenyl]urea}

The title compound was obtained employing reaction conditions identical to those described in Example 1 except that 3-aminobenzene-1,2,4-oxadiazol-5-one hydrochloride was substituted for 3-amino-(1H-tetrazol-5-yl)benzene and 3-(R)-amino-1,3-dihydro-1-methyl-5-phenyl-2H-1,4-benzodiazepin-2-one was replaced with 1,3-dihydro-1-cyclopropylmethyl-3-(R)-{[(a-methyl)-benzyloxycarbonyl]-amino}-5-phenyl-2H-1,4-benzodiazepin-2-one. Preparative thick layer chromatography of the crude reaction product on silica gel (chloroform-methanol, 96:4, v/v elution) afforded the title compound: m.p. 213° C. (d).

HPLC= >96% pure at 214 nm; TLC $R_f$=0.23 ($CHCl_3$—$CH_3OH$, 95:5).

NMR(DMSO-$D_6$): Consistent with structure assignment and confirms presence of solvent.

FAB MS: 509 ($M^+$ +1).

Analysis for $C_{28}H_{24}N_6O_4 \cdot 0.25CHCl_3$: Calculated: C, 63.02; H, 4.54; N, 15.61. Found: C, 63.12 H, 4.38; N, 15.37.

EXAMPLE 36

Synthesis of
N-{1,3-Dihydro-1-methyl-2-oxo-5-phenyl-1H-1,4-benzodiazepin-3-yl}-N'-{[3-(1,2,4-oxadiathiazol-5-one)-phenyl]urea}

3-(tert-Butyloxycarbonylamino)benzene-1,2,4-oxathiadiazol-5-one 3-(tert-Butyloxycarbonylamino)benzenylamidoxime (550 mg) was dissolved in 10 ml of pyridine and the solution was cooled to 0° C. Thionyl chloride (338.5 mg) was then added and the reaction mixture was stirred for 10 minutes. The reaction mixture was concentrated and the residue was purified by preparative thick layer chromatography on silica gel (chloroform-methanol-acetic acid, 95:5:0.5) to give the title compound.

3-Aminobenzene-1,2,4-oxathiadiazol-5-one hydrochloride

A solution of ethyl acetate (20 ml) containing 190 mg of 3-(tert-butyloxycarbonylamino)benzene-1,2,4-oxathiadiazol-5-one was cooled to 0° C. and treated with a continuous stream of hydrogen chloride gas for 10 minutes. The reaction mixture was stirred for 30 minutes more and the solvent and excess hydrogen chloride were removed under reduced pressure. The residue was azeotropically dried with toluene to give 150 mg of the title compound in sufficient purity to continue directly to the next step.

N-{1,3-Dihydro-1-methyl-2-oxo-5-phenyl-1H-1,4-benzodiazepin-3-yl}-N'-{[3-(1,2,4-oxathiadiazol-5-one)-phenyl]urea}

The title compound was obtained employing reaction conditions identical to those described in Example 22 except that 3-aminobenzene-1,2,4-oxathiadiazol-5-one hydrochloride was substituted for 3-amino-N-(acetyl)-phenylcarboxamide. Preparative thick layer chromatography of the crude reaction product on silica gel (chloroform-methanol-acetic acid-water, 90:10:1:1, v/v elution) afforded the title compound: m.p. 240° C. (d).

HPLC= >94% pure at 214 nm; TLC $R_f$=0.49 ($CH_2Cl_2$—$CH_3OH$—HOAc—$H_2O$, 90:10:1:1).

NMR(DMSO-$D_6$): Consistent with structure assignment and confirms presence of solvent.

FAB MS: 489 ($M^+$ +1).

Analysis for $C_{24}H_{20}N_6O_4S \cdot 1.45H_2O$: Calculated: C, 53.02; H, 4.25; N, 15.27. Found: C, 53.03 H, 4.09; N, 14.89.

EXAMPLE 37

Synthesis of
N-{1,3-Dihydro-1-methyl-2-oxo-5-phenyl-1H-1,4-benzodiazepin-3-yl}-N'-{[3-(1,3,4-triazol-5-one)phenyl]urea}

3-Nitrophenylhydrazinate

3-Methyl nitrobenzoate (3.0 g) was added to an ice cold solution of 15 ml of N,N-dimethylformamide containing 780 μl of hydrazine. The ice bath was removed and the reaction mixture was heated to 80° C. for 1 hour. More hydrazine was added (2 ml) and heating was continued for 30 minutes more. The reaction mixture was concentrated and azeotropically dried with toluene. The title compound (2.18 g) was obtained analytically pure after recrystallization from ethyl acetate-methanol.

3-Nitrophenyl-1,3,4-triazole-5-one

3-Nitrophenylhydrazinate (500 mg) was dissolved in 5 ml of 10% hydrogen chloride solution. The resulting solution was cooled to 0° C. and treated with a continuous stream of phosgene gas for 10 minutes. The reaction vessel was capped and stirring was continued for 1 hour more. The solids were collected and rinsed with water. Recrystallization from acetone afforded 300 mg of the title compound.

3-Aminophenyl-1,3,4-triazole-5-one

3-Nitrophenyl-1,3,4-triazole-5-one (250 mg) was dissolved in 10 ml of ethanol, treated with 0.100 g of 10% palladium/carbon catalyst, and hydrogenated on a Parr apparatus at 25 psi for 5 minutes. The reaction mixture was filtered through Celite and concentrated to give 0.160 g of the title compound.

N-{1,3-Dihydro-1-methyl-2-oxo-5-phenyl-1H-1,4-benzodiazepin-3-yl}-N'-{[3-(1,3,4-triazol-5-one)phenyl]urea}

The title compound was obtained employing reaction conditions identical to those described in Example 22 except that 3-aminobenzene-1,3,4-triazol-5-one was substituted for 3-amino-N-(acetyl)phenylcarboxamide. Preparative thick layer chromatography of the crude reaction product on silica gel (chloroform-methanol, 9:1, v/v elution) afforded the title compound: m.p. 200° C. (d).

HPLC=>95% pure at 214 nm; TLC $R_f$=0.51 ($CH_2Cl_2$—$CH_3OH$—HOAc—$H_2O$, 90:10:1:1).

NMR(DMSO-$D_6$): Consistent with structure assignment and confirms presence of solvent.

FAB MS: 469 ($M^+$ +1).

Analysis for $C_{25}H_{20}N_6O_4 \cdot 0.75H_2O \cdot 0.45$ diethyl ether: Calculated: C, 62.46; H, 5.09; N, 16.31. Found: C, 62.39 H, 4.69; N, 16.10.

What is claimed is:

1. A compound of Formula I:

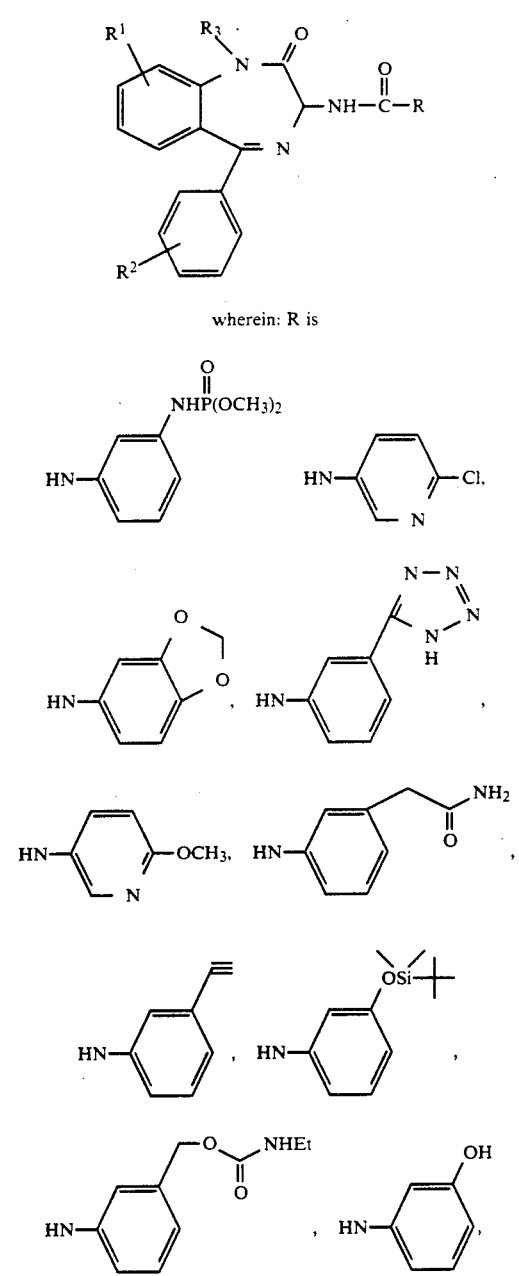

wherein: R is

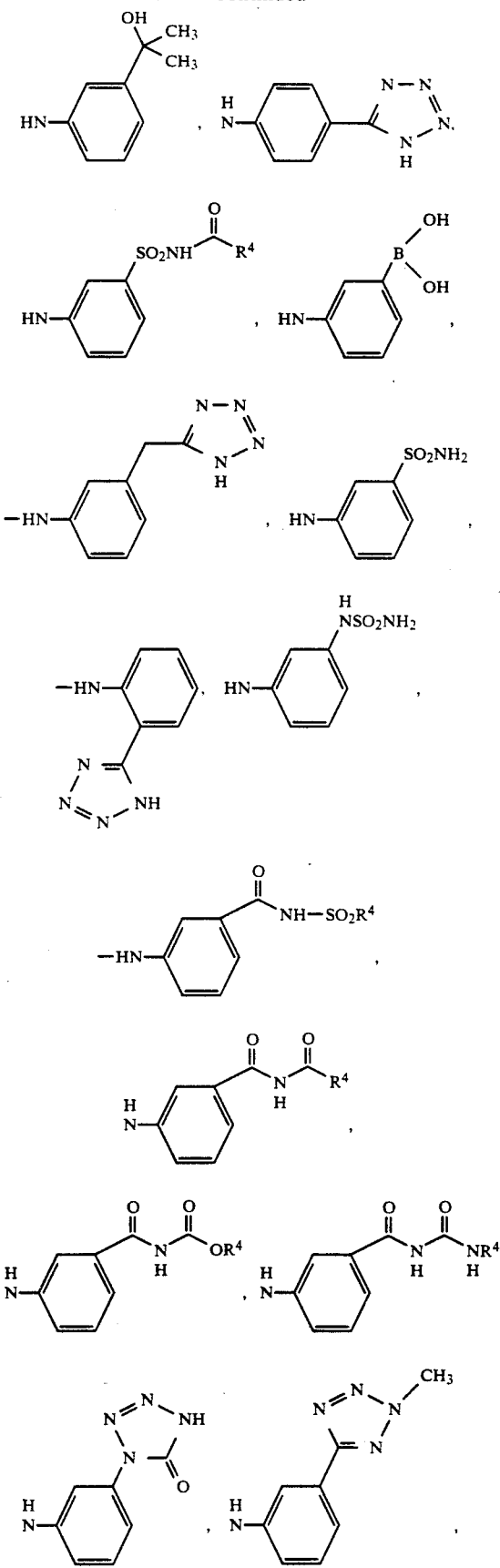

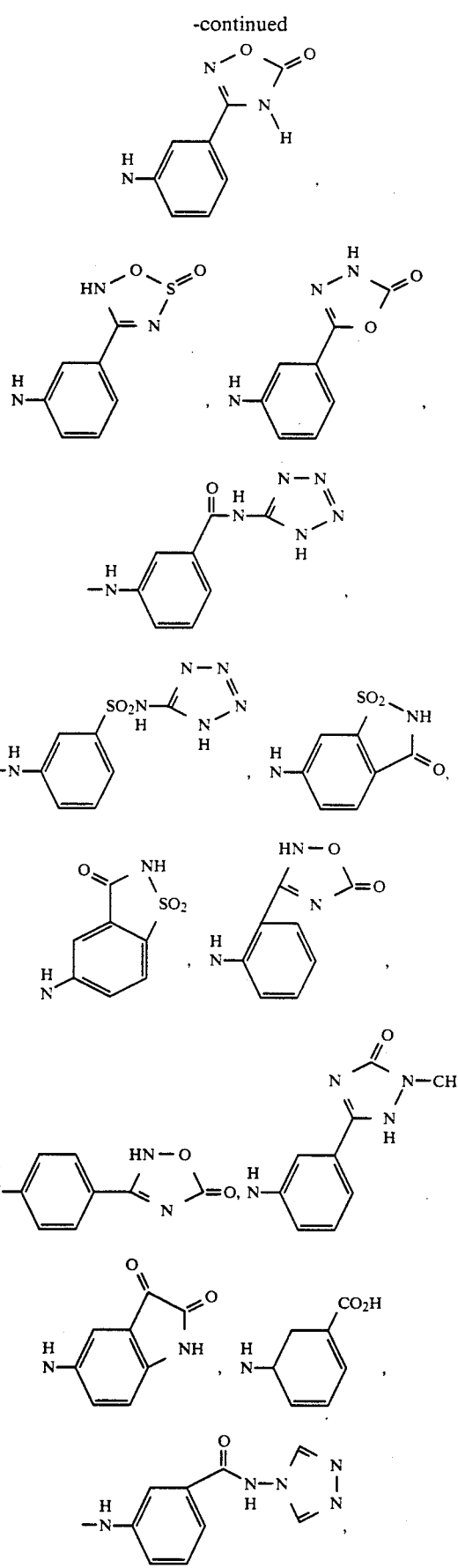
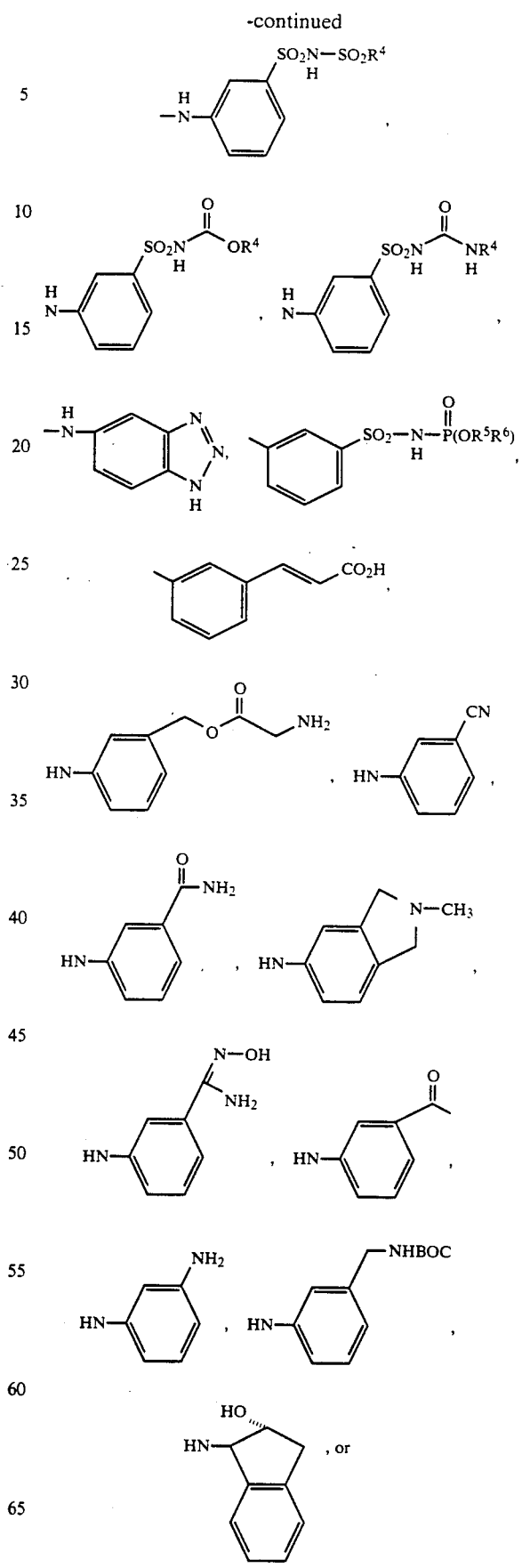

-continued

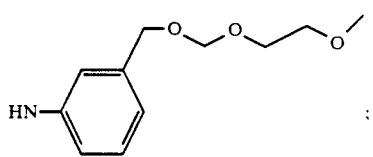

$R^1$ is absent, one or two of halogen or $CH_3$;
$R^2$ is absent, one or two of a halogen or $CH_3$;
$R^3$ is $C_1$-$C_6$ linear or branched chain alkyl or cyclopropylmethyl; and
$R^4$ is $C_1$-$C_6$ straight or branched chain alkyl, $CF_3$, cyclopropyl, 2,2-dimethylcyclopropyl, 2,2-difluorocyclopropyl, cyclobutyl, cyclopentyl, cyclohexyl, phenyl, or mono- or di-substituted phenyl wherein the substitution is F, Cl, Br, CN, $NO_2$, $CF_3$, $OCH_3$, or $NH_2$;
$R^5$ is H, methyl, ethyl, or phenyl;
$R^6$ is methyl, ethyl, or phenyl;
or the optical isomers, prodrugs or pharmaceutically acceptable salts thereof.

2. The compound of claim 1, in which the compound is:
N-{1,3-Dihydro-1-methyl-2-oxo-5-phenyl-1H-1,4-benzodiazepin-3-yl}-N'-{[3-(1H-tetrazol-5-yl)phenyl]urea},
N-{1,3-Dihydro-1-[2-methyl]propyl-2-oxo-5-phenyl-1H-1,4-benzo-diazepin-3-yl}-N'-{[3-(1H-tetrazol-5-yl)phenyl]urea},
N-{1,3-Dihydro-1-ethyl-2-oxo-5-phenyl-1H-1,4-benzodiazepin-3-yl}-N'-{[3-(1H-tetrazol-5-yl)phenyl]urea},
N-{1,3-Dihydro-1-[2-propyl]-2-oxo-5-phenyl-1H-1,4-benzodiazepin-3yl{-N'-}[3-(1H-tetrazol-5-yl)phenyl]urea},
N-{1,3-Dihydro-1-methyl-2-oxo-5-phenyl-1H-1,4-benzodiazepin-3-yl}-N'-{[5-(2-chloro)pyridyl]urea},
N-{1,3-Dihydro-1-methyl-2-oxo-5-phenyl-1H-1,4-benzodiazepin-3-yl}-N'-{[5-(2-methoxy)pyridyl]urea},
N-{1,3-Dihydro-1-methyl-2-oxo-5-phenyl-1H-1,4-benzodiazepin-3-yl}-N'-{[3-(cyano)phenyl}urea},
N-{1,3-Dihydro-1-methyl-2-oxo-5-phenyl-1H-1,4-benzodiazepin-3-yl}-N'-{[3-(acetyl)phenyl]urea},
N-{1,3-Dihydro-1-methyl-2-oxo-5phenyl-1H-1,4-benzodiazepin-3-yl}-N'-{[3-(amino)phenyl]urea},
N-{1,3-Dihydro-1-methyl-2-oxo-5-phenyl-1H-1,4-benzodiazepin-3-yl}-N'-{[3-(aminocarbonyl)phenyl]urea},
N-{1,3-Dihydro-1-methyl-2-oxo-5-phenyl-1H-1,4-benzodiazepin-3-yl}-N'-{[3-(dimethylphosphoramido),-phenyl]urea},
N-{1,3-Dihydro-1-methyl-2-oxo-5-phenyl-1H-1,4-benzodiazepin-3-yl}-N'-{[3-(aminosulfonamido)phenyl]urea},
N-{1,3-Dihydro-1-methyl-2-oxo-5-phenyl-1H-1,4-benzodiazepin-3-yl}-N'-{[benzotriazol-3-yl],urea},
N-{1,3-Dihydro-1-methyl-2-oxo-5-phenyl-1H-1,4-benzodiazepin-3-yl}-N'-{[3-(aminosulfonyl)phenyl]urea},
N-{1,3-Dihydro-1-methyl-2-oxo-5-phenyl-1H-1,4-benzodiazepin-3-yl}-N'-{[3-phenylboronyl]urea},
N-{1,3-Dihydro-1-methyl-2-oxo-5-phenyl-1H-1,4-benzodiazepin-3-yl}-N'-{[3-(acetylamino-sulfonyl)-phenyl]urea},
N-{1,3-Dihydro-1-methyl-2-oxo-5-phenyl-1H-1,4-benzodiazepin-3-yl}-N'-{[3-((1H-tetrazol-5-yl)methyl)phenyl]urea},
N-{1,3-Dihydro-1-n-propyl-2-oxo-5-phenyl-1H-1,4-benzodiazepin-3-yl}-N'-{[3-(1H-tetrazol-5-yl)phenyl]urea},
N-{1,3-Dihydro-1-(2-(S)-methylbutyl]-2-oxo-5-phenyl-1H-1,4-benzodiazepin-3-yl}-N'-{[3-(1H-tetrazol-5-yl)phenyl]urea},
N-{1,3-Dihydro-1-cyclopropylmethyl-2-oxo-5-phenyl-1H-1,4-benzodiazepin-3-yl}-N'-{[3-(1H-tetrazol-5-yl)phenyl]urea},
N-(3-(R,S)-2,3-Dihydro-5-(2-fluorophenyl)-1-(2-methylpropyl)-2-oxo-1H-1,4-benzodiazepin-3-yl]-N'-{[3-(tetrazol-5-yl)phenyl]urea}
N-{1,3-Dihydro-1-methyl-2-oxo-5-phenyl-1H-1,4-benzodiazepin-3-yl}-N'-{[3-(N-acetylcarboxamido)-phenyl]urea},
N-{1,3-Dihydro-1-methyl-2-oxo-5-phenyl-1H-1,4-benzodiazepin-3-yl}-N'-{[3-(N-(methanesulfonyl)carboxamido)phenyl]urea},
N-{1,3-Dihydro-1-methyl-2-oxo-5-phenyl-1H-1,4-benzodiazepin-3-yl}-N'-{[3-(N-(2-propylsulfonyl)carboxamido)phenyl]urea},
N-{1,3-Dihydro-1-methyl-2-oxo-5-phenyl-1H-1,4-benzodiazepin-3-yl}-N'-{[3-(N-(t-butysulfonyl)carboxamido)phenyl]urea},
N-{1,3-Dihydro-1-methyl-2-oxo-5-phenyl-1H-1,4-benzodiazepin-3-yl}-N'-{[3-(N-(2-propylaminocarbonyl)carboxamido)phenyl]urea},
N-{1,3-Dihydro-1-cyclopropylmethyl-2-oxo-5-phenyl-1H-1,4-benzodiazepin-3-yl}-N'-{[3-(N-(acetyl)sulfonamido)phenyl]urea},
N-{1,3-Dihydro-1-methyl-2-oxo-5-phenyl-1H-1,4-benzodiazepin-3-yl}-N'-{[3-(N-(1,1-dimethylethylcarbonyl)sulfonamido)phenyl]urea},
N-{1,3-Dihydro-1-methyl-2-oxo-5-phenyl-1H-1,4-benzodiazepin-3-yl}-N'-{[3-(N-(2,2-dimethylcyclopropylcarbonyl)sulfonamido)phenyl]urea},
N-{1,3-Dihydro-1-methyl-2-oxo-5-phenyl-1H-1,4-benzodiazepin-3-yl}-N'-{[3-(N-(t-butylaminocarbonyl)-sulfonamido)phenyl]urea},
N-{1,3-Dihydro-1-methyl-2-oxo-5-phenyl-1H-1,4-benzodiazepin-3-yl}-N'-{[3-(N-(diphenylphosphono)sulfonamido)phenyl]urea},
N-{1,3-Dihydro-1-methyl-2-oxo-5-phenyl-1H-1,4-benzodiazepin-3-yl}-N'-{[3-(trans-carboxyethylene)-phenyl]urea},
N-{1,3-Dihydro-1-methyl-2-oxo-5-phenyl-1H-1,4-benzodiazepin-3-yl}-N'-{[3-(2-methyltetrazol-5-yl)phenyl]urea},
N-{1,3-Dihydro-1-methyl-2-oxo-5-phenyl-1H-1,4-benzodiazepin-3-yl{-N'-}[3-(1,2,4-oxadiazol-5-one)-phenyl]urea},
N-{1,3-Dihydro-1-cyclopropylmethyl-2-oxo-5-phenyl-1H-1,4-benzodiazepin-3-yl}-N'-{[3-(1,2,4-oxadiazol-5-one)phenyl]urea},
N-{1,3-Dihydro-1-methyl-2-oxo-5-phenyl-1H-1,4-benzodiazepin-3-yl}-N'-{[3-(1,2,4-oxadiathiazol-5-one)-phenyl]urea},
N-{1,3-Dihydro-1-methyl-2-oxo-5-phenyl-1H-1,4-benzodiazepin-3-yl}-N'-{[3-(1,3,4-triazol-5-one)phenyl]urea},
or a pharmaceutically acceptable salt thereof.

3. The compound of claim 1 which is:
N-{1,3-Dihydro-1-methyl-2-oxo-5-phenyl-1H-1,4-benzodiazepin-3-yl}-N'-{[3-(1H-tetrazol-5-yl)phenyl]urea}, or a pharmaceutically acceptable salt thereof.

4. The compound of claim 1 which is:
N-{1,3-Dihydro-1-[2-methyl]propyl-2-oxo-5-phenyl-1H-1,4-benzodiazepin-3-yl}-N'-{[3-(1H-tetrazol-5- yl)phenyl]urea}, or a pharmaceutically acceptable salt thereof.

5. The compound of claim 1 which is:
N-{1,3-Dihydro-1-n-propyl-2-oxo-5-phenyl-1H-1,4-benzodiazepin-3-yl}-N'-{[3-(1H-tetrazol-5-yl)phenyl]urea}, or a pharmaceutically acceptable salt thereof.

6. The compound of claim 1 which is:
N-{1,3-Dihydro-1-methyl-2-oxo-5-phenyl-1H-1,4-benzodiazepin-3-yl}-N'-{[3-(N-(t-butyl-sulfonyl)carboxamido)phenyl]urea}, or a pharmaceutically acceptable salt thereof.

7. The compound of claim 1 which is:
N-{1,3-Dihydro-1-methyl-2-oxo-5-phenyl-1H-1,4-benzodiazepin-3-yl}-N'-{[3-(1,2,4-oxadiazol-5-one)-phenyl]urea}, or a pharmaceutically acceptable salt thereof.

8. The compound of claim 1 which is:
N-{1,3-Dihydro-1-cyclopropylmethyl-2-oxo-5-phenyl-1H-1,4-benzodiazepin-3-yl}-N'-{[3-(1,2,4-oxadiazol-5-one)phenyl]urea}, or a pharmaceutically acceptable salt thereof.

* * * * *